(12) United States Patent
Uemura et al.

(10) Patent No.: US 6,908,756 B1
(45) Date of Patent: Jun. 21, 2005

(54) SERINE PROTEASE BSSP2

(75) Inventors: Hidetoshi Uemura, Hyogo (JP); Akira Okui, Nara (JP); Katsuya Kominami, Osaka (JP); Nozomi Yamaguchi, Kyoto (JP); Shinichi Mitsui, Kyoto (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/856,371
(22) PCT Filed: Nov. 19, 1999
(86) PCT No.: PCT/JP99/06475
§ 371 (c)(1),
(2), (4) Date: May 21, 2001
(87) PCT Pub. No.: WO00/31272
PCT Pub. Date: Jun. 2, 2000

(30) Foreign Application Priority Data

Nov. 20, 1998 (JP) ............................................. 10/347785

(51) Int. Cl.[7] .......................... C12N 9/48; C12N 15/00;
C12Q 1/34; C07H 21/04
(52) U.S. Cl. ............................. 435/212; 435/4; 435/23;
435/24; 435/69.1; 435/183; 536/23.2; 536/235;
536/23.6; 536/23.7; 536/23.74
(58) Field of Search ................................ 435/212, 440,
435/4, 18; 424/94.1; 536/23.2

(56) References Cited

U.S. PATENT DOCUMENTS

2004/0048294 A1 * 3/2004 Ruben et al. .................. 435/6

FOREIGN PATENT DOCUMENTS

EP 0 949 334 10/1999

OTHER PUBLICATIONS

Kishi et al. NCBI Accession 1NPM B–1998.*
Leytus et al. A novel trypsin–like serine protease (hepsin) with a putative transmembrane domain expressed by human liver and hepatoma cells.Biochemistry. Feb. 9, 1988;27(3):1067–74.*

NCBI Accession S00845.*

Yamashiro et al., "Molecular cloning of a novel trysin–like serine protease (neurosin) preferentially expressed in brain", *Biochimica et Biophysica Acta*, (1997), pp. 11–14.

DATABASE EMBL, Jun. 7, 1999, 2 pages.

DATABASE EMBL, Oct. 13, 1997, 2 pages.

Little, S.P. et al. "Zyme, a novel and potentially amyloidogenitc enzyme CDNA isolated from Alzheimer's disease brain", The Journal of Biological Chemistry (1997) vol. 272, No. 40 pp. 25135–25142.

Yamaura, Y. et al. "Molecular cloning of a novel brain specific serine protease with a kringle–like structure and three scavenger receptor cysteine–rich motifs", Biochemical and Biophysical Research Communications (1997) vol. 239, No. 2 pp. 386–392.

Daniel, A. et al. "Excessive urokinase–type plasmino–gen-activator activity in the euglobulin fraction of patients with Alzheimer–type dementia", Journal of the Neurological Sciences (1996) vol. 139, No. 1 p. 83–88.

Hinds, T.R. et al., "Relationship between serum α1–antichymotrypsin and Alzheimer's disease", Neurobiology of Aging (1994). vol. 15, No. 1p. 21–27.

* cited by examiner

Primary Examiner—Manjunath Rao
Assistant Examiner—Yong Pak
(74) Attorney, Agent, or Firm—Browdy and Neimark, PLLC

(57) ABSTRACT

There are provided proteins having the amino acid sequences represented by SEQ ID NOS: 2, 4, 6, 8 and 10; proteins having amino acid sequences derived from these amino acid sequences by deletion, substitution or addition of one to several amino acids; and nucleotide sequences encoding the same; transgenic non-human animals with altered expression level of a serine protease BSSP2; an antibody against BSSP2; and a method for detecting BSSP2 in a specimen by using the antibody.

3 Claims, 7 Drawing Sheets

SEQUENCE LISTING

<160> NUMBER OF SEQ ID NOS: 44

<210> SEQ ID NO 1
<211> LENGTH: 717
<212> TYPE: DNA
<213> ORGANISM: Mus sp.
<220> FEATURE:
<221> NAME/KEY: CDS
<222> LOCATION: (1)..(717)
<223> OTHER INFORMATION:

<400> SEQUENCE: 1

```
ata gtt ggc ggc caa gct gtg gct tct ggg cgc tgg cca tgg caa gct        48
Ile Val Gly Gly Gln Ala Val Ala Ser Gly Arg Trp Pro Trp Gln Ala
1               5                   10                  15 agc gtg atg ctt ggc tcc cgg cac acg tgt ggg gcc tct gtg ttg gca        96
Ser Val Met Leu Gly Ser Arg His Thr Cys Gly Ala Ser Val Leu Ala
                20                  25                  30 cca cac tgg gta gtg act gct gcc cac tgc atg tac agt ttc agg ctg       144
Pro His Trp Val Val Thr Ala Ala His Cys Met Tyr Ser Phe Arg Leu
            35                  40                  45 tcc cgc cta tcc agc tgg cgg gtt cat gca ggg ctg gtc agc cat ggt       192
Ser Arg Leu Ser Ser Trp Arg Val His Ala Gly Leu Val Ser His Gly
        50                  55                  60 gct gtc cga caa cac cag gga act atg gtg gag aag atc att cct cat       240
Ala Val Arg Gln His Gln Gly Thr Met Val Glu Lys Ile Ile Pro His
65                  70                  75                  80 cct ttg tac agt gcc cag aac cat gac tat gat gtg gct ctg ctg cag       288
Pro Leu Tyr Ser Ala Gln Asn His Asp Tyr Asp Val Ala Leu Leu Gln
                85                  90                  95 ctc cgg aca cca atc aac ttc tca gac acc gtg gac gct gtg tgc ttg       336
Leu Arg Thr Pro Ile Asn Phe Ser Asp Thr Val Asp Ala Val Cys Leu
                100                 105                 110
```

```
ccg gcc aag gag cag tac ttt cca tgg ggg tcg cag tgc tgg gtg tct      384
Pro Ala Lys Glu Gln Tyr Phe Pro Trp Gly Ser Gln Cys Trp Val Ser
        115                 120                 125 ggc tgg ggc cac acc gac ccc agc cat act cat agc tca gat aca ctg      432
Gly Trp Gly His Thr Asp Pro Ser His Thr His Ser Ser Asp Thr Leu
130                 135                 140 cag gac aca atg gta ccc ctg ctc agc acc cac ctc tgc aac agc tca      480
Gln Asp Thr Met Val Pro Leu Leu Ser Thr His Leu Cys Asn Ser Ser
145                 150                 155                 160 tgc atg tac agt ggg gca ctt aca cac cgc atg ttg tgt gct ggc tac      528
Cys Met Tyr Ser Gly Ala Leu Thr His Arg Met Leu Cys Ala Gly Tyr
                165                 170                 175 ctg gat gga agg gca gac gca tgc cag gga gac agc ggg gga ccc ctg      576
Leu Asp Gly Arg Ala Asp Ala Cys Gln Gly Asp Ser Gly Gly Pro Leu
            180                 185                 190 gta tgt ccc agt ggt gac acg tgg cac ctt gta ggg gtg gtc agc tgg      624
Val Cys Pro Ser Gly Asp Thr Trp His Leu Val Gly Val Val Ser Trp
        195                 200                 205 ggt cgt ggc tgt gca gag ccc aat cgc cca ggt gtc tat gcc aag gta      672
Gly Arg Gly Cys Ala Glu Pro Asn Arg Pro Gly Val Tyr Ala Lys Val
210                 215                 220 gca gag ttc ctg gac tgg atc cat gac act gtg cag gtc cgc tag         717
Ala Glu Phe Leu Asp Trp Ile His Asp Thr Val Gln Val Arg
225                 230                 235

<210> SEQ ID NO 2
<211> LENGTH: 238
<212> TYPE: PRT
<213> ORGANISM: Mus sp.

<400> SEQUENCE: 2

Ile Val Gly Gly Gln Ala Val Ala Ser Gly Arg Trp Pro Trp Gln Ala
1               5                   10                  15

Ser Val Met Leu Gly Ser Arg His Thr Cys Gly Ala Ser Val Leu Ala
            20                  25                  30

Pro His Trp Val Val Thr Ala Ala His Cys Met Tyr Ser Phe Arg Leu
        35                  40                  45

Ser Arg Leu Ser Ser Trp Arg Val His Ala Gly Leu Val Ser His Gly
    50                  55                  60

Ala Val Arg Gln His Gln Gly Thr Met Val Glu Lys Ile Ile Pro His
65                  70                  75                  80

Pro Leu Tyr Ser Ala Gln Asn His Asp Tyr Asp Val Ala Leu Leu Gln
                85                  90                  95

Leu Arg Thr Pro Ile Asn Phe Ser Asp Thr Val Asp Ala Val Cys Leu
            100                 105                 110

Pro Ala Lys Glu Gln Tyr Phe Pro Trp Gly Ser Gln Cys Trp Val Ser
        115                 120                 125

Gly Trp Gly His Thr Asp Pro Ser His Thr His Ser Ser Asp Thr Leu
130                 135                 140

Gln Asp Thr Met Val Pro Leu Leu Ser Thr His Leu Cys Asn Ser Ser
145                 150                 155                 160

Cys Met Tyr Ser Gly Ala Leu Thr His Arg Met Leu Cys Ala Gly Tyr
                165                 170                 175

Leu Asp Gly Arg Ala Asp Ala Cys Gln Gly Asp Ser Gly Gly Pro Leu
            180                 185                 190

Val Cys Pro Ser Gly Asp Thr Trp His Leu Val Gly Val Val Ser Trp
        195                 200                 205
```

```
Gly Arg Gly Cys Ala Glu Pro Asn Arg Pro Gly Val Tyr Ala Lys Val
    210                 215                 220

Ala Glu Phe Leu Asp Trp Ile His Asp Thr Val Gln Val Arg
225                 230                 235

<210> SEQ ID NO 3
<211> LENGTH: 1685
<212> TYPE: DNA
<213> ORGANISM: Mus sp.
<220> FEATURE:
<221> NAME/KEY: CDS
<222> LOCATION: (247)..(1065)
<223> OTHER INFORMATION:
<221> NAME/KEY: mat_peptide
<222> LOCATION: (352)..()
<223> OTHER INFORMATION:

<400> SEQUENCE: 3
ctcacatgta tctttcagaa taaatggaga ggatcttctg cttcaagtac aagtaagagc      60
tcggccagac tggctcctgg tatgccatga gggccggagc ccagccctgg gcatgcacat     120
ctgcaagagt cttgggcata tcaggcttac tcaacacaag gccgtgaatc tgtctgacat     180
caagctcaac agatcccagg agtttgctca actctctgct agaccgggag gccttgtaga     240 ggaggc atg gaa gcc cag gta ggg ctt ctg tgg gtt agc gct aac tgt        288
       Met Glu Ala Gln Val Gly Leu Leu Trp Val Ser Ala Asn Cys
           -35                 -30                 -25 cct tct ggc cga att gtt tct ctc aaa tgt tct gag tgt ggg gca agg       336
Pro Ser Gly Arg Ile Val Ser Leu Lys Cys Ser Glu Cys Gly Ala Arg
        -20                 -15                 -10 cct ctg gct tct cga ata gtt ggc ggc caa gct gtg gct tct ggg cgc       384
Pro Leu Ala Ser Arg Ile Val Gly Gly Gln Ala Val Ala Ser Gly Arg
-5              -1  1               5                   10 tgg cca tgg caa gct agc gtg atg ctt ggc tcc cgg cac acg tgt ggg       432
Trp Pro Trp Gln Ala Ser Val Met Leu Gly Ser Arg His Thr Cys Gly
                15                  20                  25 gcc tct gtg ttg gca cca cac tgg gta gtg act gct gcc cac tgc atg       480
Ala Ser Val Leu Ala Pro His Trp Val Val Thr Ala Ala His Cys Met
            30                  35                  40 tac agt ttc agg ctg tcc cgc cta tcc agc tgg cgg gtt cat gca ggg       528
Tyr Ser Phe Arg Leu Ser Arg Leu Ser Ser Trp Arg Val His Ala Gly
        45                  50                  55 ctg gtc agc cat ggt gct gtc cga caa cac cag gga act atg gtg gag       576
Leu Val Ser His Gly Ala Val Arg Gln His Gln Gly Thr Met Val Glu
60                  65                  70                  75 aag atc att cct cat cct ttg tac agt gcc cag aac cat gac tat gat       624
Lys Ile Ile Pro His Pro Leu Tyr Ser Ala Gln Asn His Asp Tyr Asp
                80                  85                  90 gtg gct ctg ctg cag ctc cgg aca cca atc aac ttc tca gac acc gtg       672
Val Ala Leu Leu Gln Leu Arg Thr Pro Ile Asn Phe Ser Asp Thr Val
            95                  100                 105 gac gct gtg tgc ttg ccg gcc aag gag cag tac ttt cca tgg ggg tcg       720
Asp Ala Val Cys Leu Pro Ala Lys Glu Gln Tyr Phe Pro Trp Gly Ser
        110                 115                 120 cag tgc tgg gtg tct ggc tgg ggc cac acc gac ccc agc cat act cat       768
Gln Cys Trp Val Ser Gly Trp Gly His Thr Asp Pro Ser His Thr His
    125                 130                 135 agc tca gat aca ctg cag gac aca atg gta ccc ctg ctc agc acc cac       816
Ser Ser Asp Thr Leu Gln Asp Thr Met Val Pro Leu Leu Ser Thr His
140                 145                 150                 155 ctc tgc aac agc tca tgc atg tac agt ggg gca ctt aca cac cgc atg       864
```

-continued

| | | | | | | | | | | | | | | |
|---|---|---|---|---|---|---|---|---|---|---|---|---|---|---|
|Leu|Cys|Asn|Ser|Ser|Cys|Met|Tyr|Ser|Gly|Ala|Leu|Thr|His|Arg|Met|
| | | |160| | | |165| | | |170| | | | ttg tgt gct ggc tac ctg gat gga agg gca gac gca tgc cag gga gac       912
Leu Cys Ala Gly Tyr Leu Asp Gly Arg Ala Asp Ala Cys Gln Gly Asp
            175                 180                 185 agc ggg gga ccc ctg gta tgt ccc agt ggt gac acg tgg cac ctt gta       960
Ser Gly Gly Pro Leu Val Cys Pro Ser Gly Asp Thr Trp His Leu Val
            190                 195                 200 ggg gtg gtc agc tgg ggt cgt ggc tgt gca gag ccc aat cgc cca ggt      1008
Gly Val Val Ser Trp Gly Arg Gly Cys Ala Glu Pro Asn Arg Pro Gly
            205                 210                 215 gtc tat gcc aag gta gca gag ttc ctg gac tgg atc cat gac act gtg      1056
Val Tyr Ala Lys Val Ala Glu Phe Leu Asp Trp Ile His Asp Thr Val
220             225                 230                 235 cag gtc cgc tagccgaaga agcagcagca gccacctgtg acgccgagct              1105
Gln Val Arg gtggatcgcc catggatcac cccagtctgg gggccagcat ctgggtcact gggcctctcc    1165
ccaaaggctc tgacttcgag ttcatctttc tcatctgaga acctccacaa caggaaaagg    1225
agtctgcggc tagattggga atgatggtga gaggaaggga taggaggaca gaagagacag    1285
cagaggcttc tggaagcatc tgggagactg ctcctctgct cccccacac cccacgtgca     1345 tccactgggg gatgctggag atgcccaatc cttgtttctt gtgggccac tggaaggcta     1405 agtccaactt tagaggatgc cctgtctcga gagttactag gcagataagg ttaaggttgg    1465
acaagctcag gtaaaggcac ggaagtcaag atccctctc cccgtgcgg tcctgttctg      1525 aggtaagcta atagccccgc accaggcaga ggtctacagg gtaagaagga tgcagttggg    1585
ctacacgacg ctatttttca aatgatgttt ctgtaaattg gttgagagag ttttgttatt    1645
aaacagaaat tatgtataaa aaaaaaaaaa aaaaaaaaa                           1685

<210> SEQ ID NO 4
<211> LENGTH: 273
<212> TYPE: PRT
<213> ORGANISM: Mus sp.

<400> SEQUENCE: 4

Met Glu Ala Gln Val Gly Leu Leu Trp Val Ser Ala Asn Cys Pro Ser
-35                 -30                 -25                 -20

Gly Arg Ile Val Ser Leu Lys Cys Ser Glu Cys Gly Ala Arg Pro Leu
                -15                 -10                  -5

Ala Ser Arg Ile Val Gly Gly Gln Ala Val Ala Ser Gly Arg Trp Pro
        -1   1                   5                  10

Trp Gln Ala Ser Val Met Leu Gly Ser Arg His Thr Cys Gly Ala Ser
        15                  20                  25

Val Leu Ala Pro His Trp Val Thr Ala Ala His Cys Met Tyr Ser
30                  35                  40                  45

Phe Arg Leu Ser Arg Leu Ser Ser Trp Arg Val His Ala Gly Leu Val
                50                  55                  60

Ser His Gly Ala Val Arg Gln His Gly Thr Met Val Glu Lys Ile
                65                  70                  75

Ile Pro His Pro Leu Tyr Ser Ala Gln Asn His Asp Tyr Asp Val Ala
                80                  85                  90

Leu Leu Gln Leu Arg Thr Pro Ile Asn Phe Ser Asp Thr Val Asp Ala
                95                 100                 105

Val Cys Leu Pro Ala Lys Glu Gln Tyr Phe Pro Trp Gly Ser Gln Cys
110                 115                 120                 125

```
Trp Val Ser Gly Trp Gly His Thr Asp Pro Ser His Thr His Ser Ser
            130                 135                 140

Asp Thr Leu Gln Asp Thr Met Val Pro Leu Leu Ser Thr His Leu Cys
            145                 150                 155

Asn Ser Ser Cys Met Tyr Ser Gly Ala Leu Thr His Arg Met Leu Cys
            160                 165                 170

Ala Gly Tyr Leu Asp Gly Arg Ala Asp Ala Cys Gln Gly Asp Ser Gly
            175                 180                 185

Gly Pro Leu Val Cys Pro Ser Gly Asp Thr Trp His Leu Val Gly Val
190                 195                 200                 205

Val Ser Trp Gly Arg Gly Cys Ala Glu Pro Asn Arg Pro Gly Val Tyr
            210                 215                 220

Ala Lys Val Ala Glu Phe Leu Asp Trp Ile His Asp Thr Val Gln Val
            225                 230                 235
Arg
```

<210> SEQ ID NO 5
<211> LENGTH: 2068
<212> TYPE: DNA
<213> ORGANISM: Mus sp.
<220> FEATURE:
<221> NAME/KEY: CDS
<222> LOCATION: (516)..(1448)
<223> OTHER INFORMATION:
<221> NAME/KEY: mat_peptide
<222> LOCATION: (735)..()
<223> OTHER INFORMATION:

<400> SEQUENCE: 5

```
ctggctgggc tgttgaatca atcccgacat gaggacagga gcctcaccct gcccagcaga      60
acttactgcc ttatatcagt gcagctgact catatgagtc aacactgga tgaccaaagc     120 ccaatggaga ttcggtgcac ggaagagggt gctgggcctg ggatcttcag aatggagttg     180
ggagaccaga ggcaatccat ttctcagtcc aacgctggt gctgcctgca acgtggctgt     240
gtaatactgg gcgtcctggg gctgctggct ggagcaggca ttgcttcatg gctcttagtg     300
ttgtatctat ggccggctgc ctctccatcc atctctggga cgttgcagga ggaggagatg     360
actttgaact gtccaggagt gagctgtgag gaagagctcc ttccatctct tcccaaaaca     420
gaataaatgg aggggatctt ctgcttcaag tacaagtaag agctcggcca gactggctcc     480
tggtctgcca tgagggctgg agccccgccc tgggc atg cac atc tgc aag agt      533
                                       Met His Ile Cys Lys Ser
                                                       -70 ctt ggg cat atc agg ctt act caa cac aag gcc gtg aat ctg tct gac      581
Leu Gly His Ile Arg Leu Thr Gln His Lys Ala Val Asn Leu Ser Asp
        -65                 -60                 -55 atc aag ctc aac aga tcc cag gag ttt gct caa ctc tct gct aga ccg      629
Ile Lys Leu Asn Arg Ser Gln Glu Phe Ala Gln Leu Ser Ala Arg Pro
    -50                 -45                 -40 gga ggc ctt gta gag gag gca tgg aag ccc agc gct aac tgt cct tct      677
Gly Gly Leu Val Glu Glu Ala Trp Lys Pro Ser Ala Asn Cys Pro Ser
-35                 -30                 -25                 -20 ggc cga att gtt tct ctc aaa tgt tct gag tgt ggg gca agg cct ctg      725
Gly Arg Ile Val Ser Leu Lys Cys Ser Glu Cys Gly Ala Arg Pro Leu
            -15                 -10                 -5 gct tct cga ata gtt ggc ggc caa gct gtg gct tct ggg cgc tgg cca      773
Ala Ser Arg Ile Val Gly Gly Gln Ala Val Ala Ser Gly Arg Trp Pro
        -1  1                   5                  10 tgg caa gct agc gtg atg ctt ggc tcc cgg cac acg tgt ggg gcc tct      821
```

|   |   |
|---|---|
| Trp Gln Ala Ser Val Met Leu Gly Ser Arg His Thr Cys Gly Ala Ser<br>15 20 25 | |
| gtg ttg gca cca cac tgg gta gtg act gct gcc cac tgc atg tac agt<br>Val Leu Ala Pro His Trp Val Val Thr Ala Ala His Cys Met Tyr Ser<br>30 35 40 45 | 869 |
| ttc agg ctg tcc cgc cta tcc agc tgg cgg gtt cat gca ggg ctg gtc<br>Phe Arg Leu Ser Arg Leu Ser Ser Trp Arg Val His Ala Gly Leu Val<br>50 55 60 | 917 |
| agc cat ggt gct gtc cga caa cac cag gga act atg gtg gag aag atc<br>Ser His Gly Ala Val Arg Gln His Gln Gly Thr Met Val Glu Lys Ile<br>65 70 75 | 965 |
| att cct cat cct ttg tac agt gcc cag aac cat gac tat gat gtg gct<br>Ile Pro His Pro Leu Tyr Ser Ala Gln Asn His Asp Tyr Asp Val Ala<br>80 85 90 | 1013 |
| ctg ctg cag ctc cgg aca cca atc aac ttc tca gac acc gtg gac gct<br>Leu Leu Gln Leu Arg Thr Pro Ile Asn Phe Ser Asp Thr Val Asp Ala<br>95 100 105 | 1061 |
| gtg tgc ttg ccg gcc aag gag cag tac ttt cca tgg ggg tcg cag tgc<br>Val Cys Leu Pro Ala Lys Glu Gln Tyr Phe Pro Trp Gly Ser Gln Cys<br>110 115 120 125 | 1109 |
| tgg gtg tct ggc tgg ggc cac acc gac ccc agc cat act cat agc tca<br>Trp Val Ser Gly Trp Gly His Thr Asp Pro Ser His Thr His Ser Ser<br>130 135 140 | 1157 |
| gat aca ctg cag gac aca atg gta ccc ctg ctc agc acc cac ctc tgc<br>Asp Thr Leu Gln Asp Thr Met Val Pro Leu Leu Ser Thr His Leu Cys<br>145 150 155 | 1205 |
| aac agc tca tgc atg tac agt ggg gca ctt aca cac cgc atg ttg tgt<br>Asn Ser Ser Cys Met Tyr Ser Gly Ala Leu Thr His Arg Met Leu Cys<br>160 165 170 | 1253 |
| gct ggc tac ctg gat gga agg gca gac gca tgc cag gga gac agc ggg<br>Ala Gly Tyr Leu Asp Gly Arg Ala Asp Ala Cys Gln Gly Asp Ser Gly<br>175 180 185 | 1301 |
| gga ccc ctg gta tgt ccc agt ggt gac acg tgg cac ctt gta ggg gtg<br>Gly Pro Leu Val Cys Pro Ser Gly Asp Thr Trp His Leu Val Gly Val<br>190 195 200 205 | 1349 |
| gtc agc tgg ggt cgt ggc tgt gca gag ccc aat cgc cca ggt gtc tat<br>Val Ser Trp Gly Arg Gly Cys Ala Glu Pro Asn Arg Pro Gly Val Tyr<br>210 215 220 | 1397 |
| gcc aag gta gca gag ttc ctg gac tgg atc cat gac act gtg cag gtc<br>Ala Lys Val Ala Glu Phe Leu Asp Trp Ile His Asp Thr Val Gln Val<br>225 230 235 | 1445 |
| cgc tagccgaaga agcagcagca gccacctgtg acgccgagct gtggatcgcc<br>Arg | 1498 |
| catggatcac cccagtctgg gggccagcat ctgggtcact gggcctctcc ccaaaggctc | 1558 |
| tgacttcgag ttcatctttc tcatctgaga acctccacaa caggaaaagg agtctgcggc | 1618 |
| tagattggga atgatggtga gaggaaggga taggaggaca gaagagacag cagaggcttc | 1678 |
| tggaagcatc tgggagactg ctcctctgct cccccccacac cccacgtgca tccactgggg | 1738 |
| gatgctggag atgcccaatc cttgtttctt gtggggccac tggaaggcta agtccaactt | 1798 |
| tagaggatgc cctgtctcga gagttactag gcagataagg ttaaggttgg acaagctcag | 1858 |
| gtaaaggcac ggaagtcaag atccctctc ccccgtgcgg tcctgttctg aggtaagcta | 1918 |
| atagccccgc accaggcaga ggtctacagg gtaagaagga tgcagttggg ctacacgacg | 1978 |
| ctattttca aatgatgttt ctgtaaattg gttgagagag ttttgttatt aaacagaaat | 2038 |
| tatgtataaa aaaaaaaaaa aaaaaaaaa | 2068 |

```
<210> SEQ ID NO 6
<211> LENGTH: 311
<212> TYPE: PRT
<213> ORGANISM: Mus sp.

<400> SEQUENCE: 6

Met His Ile Cys Lys Ser Leu Gly His Ile Arg Leu Thr Gln His Lys
            -70                 -65                 -60

Ala Val Asn Leu Ser Asp Ile Lys Leu Asn Arg Ser Gln Glu Phe Ala
        -55                 -50                 -45

Gln Leu Ser Ala Arg Pro Gly Gly Leu Val Glu Glu Ala Trp Lys Pro
    -40                 -35                 -30

Ser Ala Asn Cys Pro Ser Gly Arg Ile Val Ser Leu Lys Cys Ser Glu
-25                 -20                 -15                 -10

Cys Gly Ala Arg Pro Leu Ala Ser Arg Ile Val Gly Gly Gln Ala Val
                -5                  -1  1               5

Ala Ser Gly Arg Trp Pro Trp Gln Ala Ser Val Met Leu Gly Ser Arg
        10                  15                  20

His Thr Cys Gly Ala Ser Val Leu Ala Pro His Trp Val Val Thr Ala
    25                  30                  35

Ala His Cys Met Tyr Ser Phe Arg Leu Ser Arg Leu Ser Ser Trp Arg
40                  45                  50                  55

Val His Ala Gly Leu Val Ser His Gly Ala Val Arg Gln His Gln Gly
                60                  65                  70

Thr Met Val Glu Lys Ile Ile Pro His Pro Leu Tyr Ser Ala Gln Asn
        75                  80                  85

His Asp Tyr Asp Val Ala Leu Leu Gln Leu Arg Thr Pro Ile Asn Phe
        90                  95                  100

Ser Asp Thr Val Asp Ala Val Cys Leu Pro Ala Lys Glu Gln Tyr Phe
    105                 110                 115

Pro Trp Gly Ser Gln Cys Trp Val Ser Gly Trp His Thr Asp Pro
120                 125                 130                 135

Ser His Thr His Ser Ser Asp Thr Leu Gln Asp Thr Met Val Pro Leu
            140                 145                 150

Leu Ser Thr His Leu Cys Asn Ser Ser Cys Met Tyr Ser Gly Ala Leu
            155                 160                 165

Thr His Arg Met Leu Cys Ala Gly Tyr Leu Asp Gly Arg Ala Asp Ala
            170                 175                 180

Cys Gln Gly Asp Ser Gly Gly Pro Leu Val Cys Pro Ser Gly Asp Thr
    185                 190                 195

Trp His Leu Val Gly Val Val Ser Trp Gly Arg Gly Cys Ala Glu Pro
200                 205                 210                 215

Asn Arg Pro Gly Val Tyr Ala Lys Val Ala Glu Phe Leu Asp Trp Ile
                220                 225                 230

His Asp Thr Val Gln Val Arg
            235

<210> SEQ ID NO 7
<211> LENGTH: 2070
<212> TYPE: DNA
<213> ORGANISM: Mus sp.
<220> FEATURE:
<221> NAME/KEY: CDS
<222> LOCATION: (116)..(1450)
<223> OTHER INFORMATION:
<221> NAME/KEY: mat_peptide
<222> LOCATION: (737)..()
<223> OTHER INFORMATION:
```

```
<400> SEQUENCE: 7
cccagcagaa cttactgcct tatatcagtg cagctgactc atatgccctg gtgtggggct      60
gctggatctt caaccactat ttctccagag tccaacactg gatgaccaaa gccca atg     118
                                                              Met gag att cgg tgc acg gaa gag  ggt gct ggg cct ggg  atc ttc aga        163
Glu Ile Arg Cys Thr Glu Glu  Gly Ala Gly Pro Gly  Ile Phe Arg
    -205             -200                -195 atg gag ttg gga gac cag agg  caa tcc att tct cag  tcc caa cgc        208
Met Glu Leu Gly Asp Gln Arg  Gln Ser Ile Ser Gln  Ser Gln Arg
    -190             -185                -180 tgg tgc tgc ctg caa cgt ggc  tgt gta ata ctg ggc  gtc ctg ggg        253
Trp Cys Cys Leu Gln Arg Gly  Cys Val Ile Leu Gly  Val Leu Gly
    -175             -170                -165 ctg ctg gct gga gca ggc att  gct tca tgg ctc tta  gtg ttg tat        298
Leu Leu Ala Gly Ala Gly Ile  Ala Ser Trp Leu Leu  Val Leu Tyr
    -160             -155                -150 cta tgg cca gct gcc tct cca  tcc atc tct ggg acg  ttg cag gag        343
Leu Trp Pro Ala Ala Ser Pro  Ser Ile Ser Gly Thr  Leu Gln Glu
    -145             -140                -135 gag gag atg act ttg aac tgt  cca gga gtg agc tgt  gag gaa gag        388
Glu Glu Met Thr Leu Asn Cys  Pro Gly Val Ser Cys  Glu Glu Glu
    -130             -125                -120 ctc ctt cca tct ctt ccc aaa  aca gta tct ttc aga  ata aat gga        433
Leu Leu Pro Ser Leu Pro Lys  Thr Val Ser Phe Arg  Ile Asn Gly
    -115             -110                -105 gag gat ctt ctg ctt caa gta  caa gta aga gct cgg  cca gac tgg ctc    481
Glu Asp Leu Leu Leu Gln Val  Gln Val Arg Ala Arg  Pro Asp Trp Leu
    -100             -95                 -90 ctg gtc tgc cat gag ggc tgg  agc ccc gcc ctg ggc  atg cac atc tgc    529
Leu Val Cys His Glu Gly Trp  Ser Pro Ala Leu Gly  Met His Ile Cys
-85             -80                 -75                 -70 aag agt ctt ggg cat atc agg  ctt act caa cac aag  gcc gtg aat ctg    577
Lys Ser Leu Gly His Ile Arg  Leu Thr Gln His Lys  Ala Val Asn Leu
            -65                 -60                 -55 tct gac atc aag ctc aac aga  tcc cag gag ttt gct  caa ctc tct gct    625
Ser Asp Ile Lys Leu Asn Arg  Ser Gln Glu Phe Ala  Gln Leu Ser Ala
            -50                 -45                 -40 aga ccg gga ggc ctt gta gag  gag gca tgg aag ccc  agc gct aac tgt    673
Arg Pro Gly Gly Leu Val Glu  Glu Ala Trp Lys Pro  Ser Ala Asn Cys
    -35             -30                 -25 cct tct ggc cga att gtt tct  ctc aaa tgt tct gag  tgt ggg gca agg    721
Pro Ser Gly Arg Ile Val Ser  Leu Lys Cys Ser Glu  Cys Gly Ala Arg
    -20             -15                 -10 cct ctg gct tct cga ata gtt  ggc ggc caa gct gtg  gct tct ggg cgc    769
Pro Leu Ala Ser Arg Ile Val  Gly Gly Gln Ala Val  Ala Ser Gly Arg
-5              -1  1                5                  10 tgg cca tgg caa gct agc gtg  atg ctt ggc tcc cgg  cac acg tgt ggg    817
Trp Pro Trp Gln Ala Ser Val  Met Leu Gly Ser Arg  His Thr Cys Gly
            15                  20                  25 gcc tct gtg ttg gca cca cac  tgg gta gtg act gct  gcc cac tgc atg    865
Ala Ser Val Leu Ala Pro His  Trp Val Val Thr Ala  Ala His Cys Met
            30                  35                  40 tac agt ttc agg ctg tcc cgc  cta tcc agc tgg cgg  gtt cat gca ggg    913
Tyr Ser Phe Arg Leu Ser Arg  Leu Ser Ser Trp Arg  Val His Ala Gly
            45                  50                  55 ctg gtc agc cat ggt gct gtc  cga caa cac cag gga  act atg gtg gag    961
Leu Val Ser His Gly Ala Val  Arg Gln His Gln Gly  Thr Met Val Glu
60              65                  70                  75
```

| | | |
|---|---|---|
| aag atc att cct cat cct ttg tac agt gcc cag aac cat gac tat gat | | 1009 |
| Lys Ile Ile Pro His Pro Leu Tyr Ser Ala Gln Asn His Asp Tyr Asp | | |
| 80 85 90 | | |
| gtg gct ctg ctg cag ctc cgg aca cca atc aac ttc tca gac acc gtg | | 1057 |
| Val Ala Leu Leu Gln Leu Arg Thr Pro Ile Asn Phe Ser Asp Thr Val | | |
| 95 100 105 | | |
| gac gct gtg tgc ttg ccg gcc aag gag cag tac ttt cca tgg ggg tcg | | 1105 |
| Asp Ala Val Cys Leu Pro Ala Lys Glu Gln Tyr Phe Pro Trp Gly Ser | | |
| 110 115 120 | | |
| cag tgc tgg gtg tct ggc tgg ggc cac acc gac ccc agc cat act cat | | 1153 |
| Gln Cys Trp Val Ser Gly Trp Gly His Thr Asp Pro Ser His Thr His | | |
| 125 130 135 | | |
| agc tca gat aca ctg cag gac aca atg gta ccc ctg ctc agc acc cac | | 1201 |
| Ser Ser Asp Thr Leu Gln Asp Thr Met Val Pro Leu Leu Ser Thr His | | |
| 140 145 150 155 | | |
| ctc tgc aac agc tca tgc atg tac agt ggg gca ctt aca cac cgc atg | | 1249 |
| Leu Cys Asn Ser Ser Cys Met Tyr Ser Gly Ala Leu Thr His Arg Met | | |
| 160 165 170 | | |
| ttg tgt gct ggc tac ctg gat gga agg gca gac gca tgc cag gga gac | | 1297 |
| Leu Cys Ala Gly Tyr Leu Asp Gly Arg Ala Asp Ala Cys Gln Gly Asp | | |
| 175 180 185 | | |
| agc ggg gga ccc ctg gta tgt ccc agt ggt gac acg tgg cac ctt gta | | 1345 |
| Ser Gly Gly Pro Leu Val Cys Pro Ser Gly Asp Thr Trp His Leu Val | | |
| 190 195 200 | | |
| ggg gtg gtc agc tgg ggt cgt ggc tgt gca gag ccc aat cgc cca ggt | | 1393 |
| Gly Val Val Ser Trp Gly Arg Gly Cys Ala Glu Pro Asn Arg Pro Gly | | |
| 205 210 215 | | |
| gtc tat gcc aag gta gca gag ttc ctg gac tgg atc cat gac act gtg | | 1441 |
| Val Tyr Ala Lys Val Ala Glu Phe Leu Asp Trp Ile His Asp Thr Val | | |
| 220 225 230 235 | | |
| cag gtc cgc tagccgaaga agcagcagca gccacctgtg acgccgagct | | 1490 |
| Gln Val Arg | | |
| gtggatcgcc catggatcac cccagtctgg gggccagcat ctgggtcact gggcctctcc | | 1550 |
| ccaaaggctc tgacttcgag ttcatctttc tcatctgaga acctccacaa caggaaaagg | | 1610 |
| agtctgcggc tagattggga atgatggtga gaggaaggga taggaggaca gaagagacag | | 1670 |
| cagaggcttc tggaagcatc tgggagactg ctcctctgct ccccccacac cccacgtgca | | 1730 |
| tccactgggg gatgctggag atgcccaatc cttgtttctt gtgggccac tggaaggcta | | 1790 |
| agtccaactt tagaggatgc cctgtctcga gagttactag gcagataagg ttaaggttgg | | 1850 |
| acaagctcag gtaaaggcac ggaagtcaag atccctctc ccccgtgcgg tcctgttctg | | 1910 |
| aggtaagcta atagccccgc accaggcaga ggtctacagg gtaagaagga tgcagttggg | | 1970 |
| ctacacgacg ctattttca aatgatgttt ctgtaaattg gttgagagag ttttgttatt | | 2030 |
| aaacagaaat tatgtataaa aaaaaaaaa aaaaaaaaa | | 2070 |

<210> SEQ ID NO 8
<211> LENGTH: 445
<212> TYPE: PRT
<213> ORGANISM: Mus sp.

<400> SEQUENCE: 8

Met Glu Ile Arg Cys Thr Glu Glu Gly Ala Gly Pro Gly Ile Phe
          -205              -200              -195

Arg Met Glu Leu Gly Asp Gln Arg Gln Ser Ile Ser Gln Ser Gln
          -190              -185              -180

Arg Trp Cys Cys Leu Gln Arg Gly Cys Val Ile Leu Gly Val Leu

-continued

```
                -175                -170                -165
Gly Leu Leu  Ala Gly Ala Gly Ile  Ala Ser Trp Leu Leu  Val Leu
        -160                -155                -150

Tyr Leu Trp  Pro Ala Ala Ser Pro  Ser Ile Ser Gly Thr  Leu Gln
        -145                -140                -135

Glu Glu Glu  Met Thr Leu Asn Cys  Pro Gly Val Ser Cys  Glu Glu
        -130                -125                -120

Glu Leu Leu  Pro Ser Leu Pro Lys  Thr Val Ser Phe Arg  Ile Asn
        -115                -110                -105

Gly Glu Asp  Leu Leu Leu Gln Val  Gln Val Arg Ala Arg  Pro Asp Trp
        -100                 -95                 -90

Leu Leu Val  Cys His Glu Gly Trp  Ser Pro Ala Leu Gly  Met His Ile
         -85                 -80                 -75

Cys Lys Ser  Leu Gly His Ile Arg  Leu Thr Gln His Lys  Ala Val Asn
-70              -65                 -60                      -55

Leu Ser Asp  Ile Lys Leu Asn Arg  Ser Gln Glu Phe Ala  Gln Leu Ser
         -50                 -45                 -40

Ala Arg Pro  Gly Gly Leu Val Glu  Glu Ala Trp Lys Pro  Ser Ala Asn
         -35                 -30                 -25

Cys Pro Ser  Gly Arg Ile Val Ser  Leu Lys Cys Ser Glu  Cys Gly Ala
         -20                 -15                 -10

Arg Pro Leu  Ala Ser Arg Ile Val  Gly Gly Gln Ala Val  Ala Ser Gly
          -5        -1   1                   5                  10

Arg Trp Pro  Trp Gln Ala Ser Val  Met Leu Gly Ser Arg  His Thr Cys
          15                  20                  25

Gly Ala Ser  Val Leu Ala Pro His  Trp Val Val Thr Ala  Ala His Cys
          30                  35                  40

Met Tyr Ser  Phe Arg Leu Ser Arg  Leu Ser Ser Trp Arg  Val His Ala
          45                  50                  55

Gly Leu Val  Ser His Gly Ala Val  Arg Gln His Gln Gly  Thr Met Val
          60                  65                  70

Glu Lys Ile  Ile Pro His Pro Leu  Tyr Ser Ala Gln Asn  His Asp Tyr
75                    80                  85                  90

Asp Val Ala  Leu Leu Gln Leu Arg  Thr Pro Ile Asn Phe  Ser Asp Thr
          95                 100                 105

Val Asp Ala  Val Cys Leu Pro Ala  Lys Glu Gln Tyr Phe  Pro Trp Gly
         110                 115                 120

Ser Gln Cys  Trp Val Ser Gly Trp  Gly His Thr Asp Pro  Ser His Thr
         125                 130                 135

His Ser Ser  Asp Thr Leu Gln Asp  Thr Met Val Pro Leu  Leu Ser Thr
         140                 145                 150

His Leu Cys  Asn Ser Ser Cys Met  Tyr Ser Gly Ala Leu  Thr His Arg
155                 160                 165                     170

Met Leu Cys  Ala Gly Tyr Leu Asp  Gly Arg Ala Asp Ala  Cys Gln Gly
             175                 180                 185

Asp Ser Gly  Gly Pro Leu Val Cys  Pro Ser Gly Asp Thr  Trp His Leu
         190                 195                 200

Val Gly Val  Val Ser Trp Gly Arg  Gly Cys Ala Glu Pro  Asn Arg Pro
         205                 210                 215

Gly Val Tyr  Ala Lys Val Ala Glu  Phe Leu Asp Trp Ile  His Asp Thr
         220                 225                 230

Val Gln Val Arg
235
```

```
<210> SEQ ID NO 9
<211> LENGTH: 2265
<212> TYPE: DNA
<213> ORGANISM: Homo sapiens
<220> FEATURE:
<221> NAME/KEY: CDS
<222> LOCATION: (156)..(1526)
<223> OTHER INFORMATION:
<221> NAME/KEY: mat_peptide
<222> LOCATION: (807)..()
<223> OTHER INFORMATION:

<400> SEQUENCE: 9
```

| | | |
|---|---|---|
| acgcgggata cagggagggg ccatgtgcga accagggaga cctcatcttc caaccaagct | | 60 |
| tgctgggctt gcatttaatc aatgcatggc cagagaacag gagcggaaca ttgcctagta | | 120 |
| gaccctgagg ctttacaaca gtgctactga cccct atg agc ctg atg ctg gat<br>                                             Met Ser Leu Met Leu Asp<br>                                                -215 | | 173 |
| gac caa ccc cct atg gag gcc cag tat gca gag gag ggc cca gga<br>Asp Gln Pro Pro Met Glu Ala Gln Tyr Ala Glu Glu Gly Pro Gly<br>    -210                   -205                   -200 | | 218 |
| cct ggg atc ttc aga gca gag cct gga gac cag cag cat ccc att<br>Pro Gly Ile Phe Arg Ala Glu Pro Gly Asp Gln Gln His Pro Ile<br>-195                 -190                   -185 | | 263 |
| tct cag gcg gtg tgc tgg cgt tcc atg cga cgt ggc tgt gca gtg<br>Ser Gln Ala Val Cys Trp Arg Ser Met Arg Arg Gly Cys Ala Val<br>    -180                   -175                   -170 | | 308 |
| ctg gga gcc ctg ggg ctg ctg gcc ggt gca ggt gtt ggc tca tgg<br>Leu Gly Ala Leu Gly Leu Leu Ala Gly Ala Gly Val Gly Ser Trp<br>-165                 -160                   -155 | | 353 |
| ctc cta gtg ctg tat ctg tgt cct gct gcc tct cag ccc att tcc<br>Leu Leu Val Leu Tyr Leu Cys Pro Ala Ala Ser Gln Pro Ile Ser<br>    -150                   -145                   -140 | | 398 |
| ggg acc ttg cag gat gag gag ata act ttg agc tgc tca gag gcc<br>Gly Thr Leu Gln Asp Glu Glu Ile Thr Leu Ser Cys Ser Glu Ala<br>-135                 -130                   -125 | | 443 |
| agc gct gag gaa gct ctg ctc cct gca ctc ccc aaa aca gta tct<br>Ser Ala Glu Glu Ala Leu Leu Pro Ala Leu Pro Lys Thr Val Ser<br>    -120                   -115                   -110 | | 488 |
| ttc aga ata aac agc gaa gac ttc ttg ctg gaa gcg caa gtg agg gat<br>Phe Arg Ile Asn Ser Glu Asp Phe Leu Leu Glu Ala Gln Val Arg Asp<br>-105                 -100                   -95 | | 536 |
| cag cca cgc tgg ctc ctg gtc tgc cat gag ggc tgg agc ccc gcc ctg<br>Gln Pro Arg Trp Leu Leu Val Cys His Glu Gly Trp Ser Pro Ala Leu<br>-90                -85                -80                -75 | | 584 |
| ggg ctg cag atc tgc tgg agc ctt ggc cat ctc aga ctc act cac cac<br>Gly Leu Gln Ile Cys Trp Ser Leu Gly His Leu Arg Leu Thr His His<br>            -70                -65                -60 | | 632 |
| aag gga gta aac ctc act gac atc aaa ctc aac agt tcc cag gag ttt<br>Lys Gly Val Asn Leu Thr Asp Ile Lys Leu Asn Ser Ser Gln Glu Phe<br>              -55                -50                -45 | | 680 |
| gct cag ctc tct cct aga ctg gga ggc ttc ctg gag gag gcg tgg cag<br>Ala Gln Leu Ser Pro Arg Leu Gly Gly Phe Leu Glu Glu Ala Trp Gln<br>        -40                -35                -30 | | 728 |
| ccc agg aac aac tgc act tct ggt caa gtt gtt tcc ctc aga tgc tct<br>Pro Arg Asn Asn Cys Thr Ser Gly Gln Val Val Ser Leu Arg Cys Ser<br>       -25                  -20                  -15 | | 776 |
| gag tgt gga gcg agg ccc ctg gct tcc cgg ata gtt ggt ggg cag tct<br>Glu Cys Gly Ala Arg Pro Leu Ala Ser Arg Ile Val Gly Gly Gln Ser<br>-10                 -5                 -1  1                   5 | | 824 |

-continued

| | |
|---|---|
| gtg gct cct ggg cgc tgg ccg tgg cag gcc agc gtg gcc ctg ggc ttc<br>Val Ala Pro Gly Arg Trp Pro Trp Gln Ala Ser Val Ala Leu Gly Phe<br>           10                     15                      20 | 872 |
| cgg cac acg tgt ggg ggc tct gtg cta gcg cca cgc tgg gtg gtg act<br>Arg His Thr Cys Gly Gly Ser Val Leu Ala Pro Arg Trp Val Val Thr<br>          25                      30                      35 | 920 |
| gct gca cat tgt atg cac agt ttc agg ctg gcc cgc ctg tcc agc tgg<br>Ala Ala His Cys Met His Ser Phe Arg Leu Ala Arg Leu Ser Ser Trp<br>         40                       45                    50 | 968 |
| cgg gtt cat gcg ggg ctg gtc agc cac agt gcc gtc agg ccc cac caa<br>Arg Val His Ala Gly Leu Val Ser His Ser Ala Val Arg Pro His Gln<br>55                      60                      65                    70 | 1016 |
| ggg gct ctg gtg gag agg att atc cca cac ccc ctc tac agt gcc cag<br>Gly Ala Leu Val Glu Arg Ile Ile Pro His Pro Leu Tyr Ser Ala Gln<br>                      75                      80                      85 | 1064 |
| aat cat gac tac gac gtc gcc ctc ctg agg ctc cag acc gct ctc aac<br>Asn His Asp Tyr Asp Val Ala Leu Leu Arg Leu Gln Thr Ala Leu Asn<br>         90                       95                      100 | 1112 |
| ttc tca gac act gtg ggc gct gtg tgc ctg ccg gcc aag gaa cag cat<br>Phe Ser Asp Thr Val Gly Ala Val Cys Leu Pro Ala Lys Glu Gln His<br>          105                     110                     115 | 1160 |
| ttt ccg aag ggc tcg cgg tgc tgg gtg tct ggc tgg ggc cac acc cac<br>Phe Pro Lys Gly Ser Arg Cys Trp Val Ser Gly Trp Gly His Thr His<br>120                      125                     130 | 1208 |
| cct agc cat act tac agc tcg gat atg ctc cag gac acg gtg gtg ccc<br>Pro Ser His Thr Tyr Ser Ser Asp Met Leu Gln Asp Thr Val Val Pro<br>135                      140                     145                     150 | 1256 |
| ttg ttc agc act cag ctc tgc aac agc tct tgc gtg tac agc gga gcc<br>Leu Phe Ser Thr Gln Leu Cys Asn Ser Ser Cys Val Tyr Ser Gly Ala<br>                     155                     160                     165 | 1304 |
| ctc acc ccc cgc atg ctt tgc gct ggc tac ctg gac gga agg gct gat<br>Leu Thr Pro Arg Met Leu Cys Ala Gly Tyr Leu Asp Gly Arg Ala Asp<br>                   170                     175                     180 | 1352 |
| gca tgc cag gga gat agc ggg ggc ccc cta gtg tgc cca gat ggg gac<br>Ala Cys Gln Gly Asp Ser Gly Gly Pro Leu Val Cys Pro Asp Gly Asp<br>          185                     190                     195 | 1400 |
| aca tgg cgc cta gtg ggg gtg gtc agc tgg ggg cgt gcg tgc gca gag<br>Thr Trp Arg Leu Val Gly Val Val Ser Trp Gly Arg Ala Cys Ala Glu<br>200                      205                     210 | 1448 |
| ccc aat cac cca ggt gtc tac gcc aag gta gct gag ttt ctg gac tgg<br>Pro Asn His Pro Gly Val Tyr Ala Lys Val Ala Glu Phe Leu Asp Trp<br>215                      220                     225                     230 | 1496 |
| atc cat gac act gct cag gac tcc ctc ctc tgagtcctgc tgtttcctcc<br>Ile His Asp Thr Ala Gln Asp Ser Leu Leu<br>                   235                     240 | 1546 |
| agtctcactg cacaccactg cctcatgctt cctggggcct ccagcagctc cactaatgga | 1606 |
| ggagaggcag tagcctccga cacagaacgc atggacctcc tactactgtg tgtgaggaac | 1666 |
| agtcactacc cactggccag ccacccagcc aacaggtctc tcctcttggg ccctgatttc | 1726 |
| agatccctct ttctcactag agactcaatg acagaagaga ggctgggact tggttgggca | 1786 |
| tgctgtggtt gctgagggat gaggggagg agagaggtag gagctggaga tgaagagact | 1846 |
| gctagaagca gcaggaagcc tgcccttctg ccctctcccc tccctgcccc tgtgtgagtc | 1906 |
| ttttagggag ggtgactggg aggtgccccc cgtcccacct ttttcctgtg ctctaggtgg | 1966 |
| gctaagtgcc tccctagagg actccatggc tgagaggctc ctgggcagat ggggtcaagg | 2026 |
| ctgggccagt cccagatgaa gcctatggga gtcaggaccc tctccactct ccctctccac | 2086 |

```
tccccttcct gttctcacct ggctgtggct ggccctgtgt ggggtgggta cactggaaaa    2146
caagaaggtt ggagttggtc taggacattg gttttaaatg acagttctgt gaactggtcc    2206
aaggaggttc tgttattaaa gtgatatatg gtcttgaaaa aaaaaaaaa aaaaaaaa      2265
```

<210> SEQ ID NO 10
<211> LENGTH: 457
<212> TYPE: PRT
<213> ORGANISM: Homo sapiens

<400> SEQUENCE: 10

```
Met Ser Leu  Met Leu Asp Asp Gln  Pro Pro Met Glu Ala  Gln Tyr
        -215              -210               -205

Ala Glu Glu  Gly Pro Gly Pro Gly  Ile Phe Arg Ala Glu  Pro Gly
        -200              -195               -190

Asp Gln Gln  His Pro Ile Ser Gln  Ala Val Cys Trp Arg  Ser Met
        -185              -180               -175

Arg Arg Gly  Cys Ala Val Leu Gly  Ala Leu Gly Leu Leu  Ala Gly
        -170              -165               -160

Ala Gly Val  Gly Ser Trp Leu Leu  Val Leu Tyr Leu Cys  Pro Ala
        -155              -150               -145

Ala Ser Gln  Pro Ile Ser Gly Thr  Leu Gln Asp Glu Glu  Ile Thr
        -140              -135               -130

Leu Ser Cys  Ser Glu Ala Ser Ala  Glu Glu Ala Leu Leu  Pro Ala
        -125              -120               -115

Leu Pro Lys  Thr Val Ser Phe Arg  Ile Asn Ser Glu Asp  Phe Leu
        -110              -105               -100

Leu Glu Ala Gln Val Arg Asp Gln  Pro Arg Trp Leu Leu Val Cys His
        -95              -90              -85

Glu Gly Trp Ser Pro Ala Leu Gly  Leu Gln Ile Cys Trp Ser Leu Gly
    -80              -75               -70

His Leu Arg Leu Thr His His Lys  Gly Val Asn Leu Thr Asp Ile Lys
-65              -60              -55              -50

Leu Asn Ser Ser Gln Glu Phe Ala  Gln Leu Ser Pro Arg Leu Gly Gly
                -45               -40              -35

Phe Leu Glu Glu Ala Trp Gln Pro  Arg Asn Asn Cys Thr Ser Gly Gln
            -30              -25               -20

Val Val Ser Leu Arg Cys Ser Glu  Cys Gly Ala Arg Pro Leu Ala Ser
        -15              -10               -5

Arg Ile Val Gly Gly Ser Val Ala  Pro Gly Arg Trp Pro Trp Gln
 -1  1                5              10              15

Ala Ser Val Ala Leu Gly Phe Arg  His Thr Cys Gly Gly Ser Val Leu
                 20               25              30

Ala Pro Arg Trp Val Val Thr Ala  Ala His Cys Met His Ser Phe Arg
             35               40               45

Leu Ala Arg Leu Ser Ser Trp Arg  Val His Ala Gly Leu Val Ser His
         50               55               60

Ser Ala Val Arg Pro His Gln Gly  Ala Leu Val Glu Arg Ile Ile Pro
 65               70               75

His Pro Leu Tyr Ser Ala Gln Asn  His Asp Tyr Asp Val Ala Leu Leu
 80               85               90               95

Arg Leu Gln Thr Ala Leu Asn Phe  Ser Asp Thr Val Gly Ala Val Cys
             100              105              110

Leu Pro Ala Lys Glu Gln His Phe  Pro Lys Gly Ser Arg Cys Trp Val
         115              120              125
```

```
Ser Gly Trp Gly His Thr His Pro Ser His Thr Tyr Ser Ser Asp Met
        130                 135                 140

Leu Gln Asp Thr Val Val Pro Leu Phe Ser Thr Gln Leu Cys Asn Ser
    145                 150                 155

Ser Cys Val Tyr Ser Gly Ala Leu Thr Pro Arg Met Leu Cys Ala Gly
160                 165                 170                 175

Tyr Leu Asp Gly Arg Ala Asp Ala Cys Gln Gly Asp Ser Gly Gly Pro
                180                 185                 190

Leu Val Cys Pro Asp Gly Asp Thr Trp Arg Leu Val Gly Val Val Ser
            195                 200                 205

Trp Gly Arg Ala Cys Ala Glu Pro Asn His Pro Gly Val Tyr Ala Lys
        210                 215                 220

Val Ala Glu Phe Leu Asp Trp Ile His Asp Thr Ala Gln Asp Ser Leu
    225                 230                 235

Leu
240

<210> SEQ ID NO 11
<211> LENGTH: 99
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pSecTrypHis

<400> SEQUENCE: 11
aagcttggct agcaacacca tgaatctact cctgatcctt acctttgttg ctgctgctgt      60
tgctgccccc tttgacgacg atgacaagga tccgaattc                            99

<210> SEQ ID NO 12
<211> LENGTH: 99
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pSecTrypHis

<400> SEQUENCE: 12
gaattcggat ccttgtcatc gtcgtcaaag ggggcagcaa cagcagcagc aacaaaggta      60
aggatcagga gtagattcat ggtgttgcta gccaagctt                            99

<210> SEQ ID NO 13
<211> LENGTH: 15
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer t amplify
      neurosin-encoding sequence

<400> SEQUENCE: 13
ttggtgcatg gcgga                                                      15

<210> SEQ ID NO 14
<211> LENGTH: 27
<212> TYPE: DNA
<213> ORGANISM: Artificial Sequence
```

```
<220> FEATURE:
<223> OTHER INFORMATION: Synthetic
<221> NAME/KEY: misc_feature
<223> OTHER INFORMATION: Designed oligonucleotide primer to amplify
      neurosin-encoding sequence

<400> SEQUENCE: 14
tcctcgagac ttggcctgaa tggtttt                                            27

<210> SEQ ID NO 15
<211> LENGTH: 35
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid p SecTrypHis/Neurosin

<400> SEQUENCE: 15
gcgctagcag atctccatga atctactcct gatcc                                   35

<210> SEQ ID NO 16
<211> LENGTH: 29
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid p SecTrypHis/Neurosin

<400> SEQUENCE: 16
tgaagcttgc catggaccaa cttgtcatc                                          29

<210> SEQ ID NO 17
<211> LENGTH: 26
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid p TrypHis

<400> SEQUENCE: 17
ccaagcttca ccatcaccat caccat                                             26

<210> SEQ ID NO 18
<211> LENGTH: 17
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
      portion of plasmid p TrypSigTag

<400> SEQUENCE: 18
gcacagtcga ggctgat                                                       17

<210> SEQ ID NO 19
<211> LENGTH: 17
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify a
```

-continued portion of plasmid p FBTrypSigTag

<400> SEQUENCE: 19
caaatgtggt atggctg                                                   17

<210> SEQ ID NO 20
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify
      conserved region of serin proteases-encoding sequence
<221> NAME/KEY: misc_feature
<222> LOCATION: (9)..(9)
<223> OTHER INFORMATION: n is a, c, g or t.
<221> NAME/KEY: misc_feature
<222> LOCATION: (12)..(12)
<223> OTHER INFORMATION: n is a, c, g or t.

<400> SEQUENCE: 20
gtgctcacng cngcbcaytg                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer to amplify
      conserved region of serin proteases-encoding sequence
<221> NAME/KEY: misc_feature
<222> LOCATION: (12)..(12)
<223> OTHER INFORMATION: n is a, c, g or t.
<221> NAME/KEY: misc_feature
<222> LOCATION: (15)..(15)
<223> OTHER INFORMATION: n is a, c, g or t.

<400> SEQUENCE: 21
ccvctrwsdc cnccnggcga                                                20

<210> SEQ ID NO 22
<211> LENGTH: 21
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSP2.0 for RACE for mBSSP2 (forward)

<400> SEQUENCE: 22
atggtggaga agatcattcc t                                              21

<210> SEQ ID NO 23
<211> LENGTH: 19
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSP2.1 for RACE for mBSSP2 (forward)

<400> SEQUENCE: 23
tacagtgccc agaaccatg                                                 19

```
<210> SEQ ID NO 24
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSPF4 for RACE for mBSSP2 (forward)

<400> SEQUENCE: 24
ctcaactctc tgctagaccg                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSP2F5 toamplify mature mBSSP2-encoding region (forward)

<400> SEQUENCE: 25
atagttggcg gccaagctgt                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSP2.2 for RACE for mBSSP2 (reverse)

<400> SEQUENCE: 26
cccagcagaa cttactgcct                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSP2E2 for RACE for mBSSP2 (reverse)

<400> SEQUENCE: 27
tgttgcagag gtgggtgctg                                               20

<210> SEQ ID NO 28
<211> LENGTH: 21
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSP2R2 for RACE for mBSSP2 (reverse)

<400> SEQUENCE: 28
taccattgtg tcctgcagtg t                                             21

<210> SEQ ID NO 29
<211> LENGTH: 27
<212> TYPE: DNA
```

```
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      mBSSP2R5/E to amplify full-length mBSSP2-encoding mRNA (reverse)

<400> SEQUENCE: 29
tgaattctgc tgcttcttcg gctagcg                                          27

<210> SEQ ID NO 30
<211> LENGTH: 18
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      BSSP2SPF to amplify a portion of hBSSP2 (forward)

<400> SEQUENCE: 30
actgctgccc actgcatg                                                    18

<210> SEQ ID NO 31
<211> LENGTH: 21
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      BSSP2SPR to amplify a portion of hBSSP2 (reverse)

<400> SEQUENCE: 31
cagggdtccc ccgctgtctc c                                                21

<210> SEQ ID NO 32
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      hBSSP2F11 for RACE for hBSSP2 (forward)

<400> SEQUENCE: 32
gctctcaact tctcagacac                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      hBSSP2R12 for RACE for hBSSP2 (reverse)

<400> SEQUENCE: 33
actcagctac cttggcgtag                                                  20

<210> SEQ ID NO 34
<211> LENGTH: 20
<212> TYPE: DNA
<213> ORGANISM: Artificial Sequence
<220> FEATURE:
<223> OTHER INFORMATION: Synthetic
<221> NAME/KEY: misc_feature
```

```
<223> OTHER INFORMATION: Designed oligonucleotide primer designated as
      hBSSP2R11 for RACE for hBSSP2 (reverse)

<400> SEQUENCE: 34
cctggagcat atccgagctg                                                      20

<210> SEQ ID NO 35
<211> LENGTH: 18
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      hBSSP2F12 to amplify full length hBSSP2 (forward)

<400> SEQUENCE: 35
gctttacaac agtgctac                                                        18

<210> SEQ ID NO 36
<211> LENGTH: 28
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      hBSSP2R13/E to amplify full length hBSSP2 (reverse)

<400> SEQUENCE: 36
tggaattcga ggaaacagca ggactcag                                             28

<210> SEQ ID NO 37
<211> LENGTH: 19
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer for RACE for
      hBSSP2

<400> SEQUENCE: 37
tactagtcga cgcgtggcc                                                       19

<210> SEQ ID NO 38
<211> LENGTH: 18
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      hBSSP2F13 to amplify a portion of hBSSP2 (forward)

<400> SEQUENCE: 38
actgctgccc actgcatg                                                        18

<210> SEQ ID NO 39
<211> LENGTH: 35
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide primer designated as
      FBTrpsigtagF5 to detect hBSSP2

<400> SEQUENCE: 39
```

```
<210> SEQ ID NO 40
<211> LENGTH: 117
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pTrypHis

<400> SEQUENCE: 40
aagcttggct agcaacacca tgaatctact cctgatcctt acctttgttg ctgctgctgt    60
tgctgccccc tttcaccatc accatcacca tgacgacgat gacaaggatc cgaattc     117

<210> SEQ ID NO 41
<211> LENGTH: 117
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Designed oligonucleotide to construct plasmid
      pTrypHis

<400> SEQUENCE: 41
gaattcggat ccttgtcatc gtcgtcatgg tgatggtgat ggtgaaaggg ggcagcaaca    60
gcagcagcaa caaaggtaag gatcaggagt agattcatgg tgttgctagc caagctt     117

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Asp Asp Asp Asp Lys
1               5

<210> SEQ ID NO 43
<211> LENGTH: 4
<212> TYPE: PRT
<213> ORGANISM: Artificial Sequence
<220> FEATURE:
<223> OTHER INFORMATION: Synthetic

<400> SEQUENCE: 43

Leu Val His Gly
1

<210> SEQ ID NO 44
<211> LENGTH: 37
<212> TYPE: DNA
<213> ORGANISM: Artificial Sequence
<220> FEATURE:
<223> OTHER INFORMATION: Synthetic

<400> SEQUENCE: 44
ggccacgcgt cgactagtac tttttttttt ttttttt                              37
```

SERINE PROTEASE BSSP2

REFERENCE TO RELATED APPLICATIONS

The present application is the national stage under 35 U.S.C. §371 of international application PCT/JP99/06475, filed 19 Nov. 1999 which designated the United States, and which application was not published in the English language.

FIELD OF THE INVENTION

The present invention relates to isolated polynucleotides of human and mouse serine proteases (hereinafter referred to as "hBSSP2" and "mBSSP2", respectively, and, in case no differentiation thereof from each other is needed, simply referred to as "BSSP2"), and their homologous forms, mature forms, precursors and polymorphic variants as well as a method for detecting thereof. Further, it relates to hBSSP2 and mBSSP2 proteins, compositions containing hBSSP2 and mBSSP2 polynucleotides and proteins, as well as their production and use.

BACKGROUND OF THE INVENTION

In general, proteases are biosynthesized as inactive precursors. They undergo limited hydrolysis in molecules to be converted into activated type proteases. In so far as enzymes are proteases, they have an activity for hydrolyzing a peptide bond, while their actions vary according to kinds of proteases. According to a particular kind of catalytic site, proteases are divided into serine proteases, cysteine proteases, aspartate proteases, metal proteases and the like. Proteases of each kind have a variety of properties, ranging from a protease having general digestive properties to a protease having various regulatory domains and strict substrate specificity, thereby specifically hydrolyzing only characteristic proteins.

Further, proteins undergo various types of processing even after translation to produce active proteins. In many secretory proteins, a protein is first synthesized on the ribosome in cytoplasm as an inactive precursor (pro-form) which comprises an active protein bearing at the N-terminus thereof a peptide of about 15 to 60 amino acids responsible for secretion (secretory signal). This peptide region is concerned with the mechanism for passing through the cell membrane and is removed upon cleavage by a specific protease during the passage through the membrane, in almost all the cases, to produce the mature form. A secretory signal has a broad hydrophobic region comprising hydrophobic amino acids in the middle of the sequence, and basic amino acid residues at a site close to the N-terminus. A secretory signal is a synonym for a signal peptide. In addition, in some proteins, a peptide moiety which functions as a secretory signal is further attached to the N-terminus of the inactive precursor (pro-form). Such a protein is called a prepro-protein (prepro-form).

For example, trypsin is present in the form of a preproform immediately after translation into amino acids. After being secreted from cells, it is present in the form of a pro-form and is then converted into active trypsin in the duodenum upon limited hydrolysis by enteropeptidase or by trypsin itself.

The optimal pH range of serine proteases is neutral to weak alkaline and, in general, many at them have a molecular weight of about 30,000 or lower. All proteases relating to blood coagulation, fibrinolysis and complement systems having a large molecular weight belong to the family of trypsin-like serine proteases. They have many regulator domains and form a protease cascade which is of very importance to reactions in a living body.

Recently, cDNAs and amino acid sequences of many novel proteases have been determined by PCR for consensus sequences of serine proteases using oligonucleotide primers. According to this method, novel proteases have been found by various researchers such as Yamamura et al. (Yamamura, Y et al., Biochem. Biophys. Res. Commun., 239, 386, 1997), Gschwend, et al. (Gschwend, T. P. et al., Mol. Cell. Neurosci., 9. 207, 1997), Chen et al. (Chen, Z-L, et al., J. Neurosci., 15, 5088, 1995) and others.

SEQ ID NO: 3 of JP 9-149790 A discloses neurosin as a novel serine protease. Neurosin has also been reported in Biochimica et Byophysica Acta, 1350, 11–14, 1997. By this, there is provided a method for mass production of neurosin using the serine protease gene and a method for screening specific inhibitors using the enzyme. In addition, the screening method has been shown to be useful for screening medicines for treating various diseases.

Serine proteases expressed in a brain-nerve system such as neurosin are considered to play various roles in the brain-nerve system. Therefore, there is a possibility that isolation of a gene encoding a novel protease expressed in a brain-nerve system and production of a protein using the gene would be useful for diagnosis or therapy of various diseases related to the brain-nerve system.

Nowadays, in general, clinical diagnosis of Alzheimer's disease is based on the diagnosis standard of DSM-IIIR and NINCDS-ADRDA (Mckhann, G. et al., Neurology, 34, 939, 1994) or the diagnosis standard of DSM-IV (American Psychiatric Association; Diagnostic and statistical manuals of mental disorders, 4th ed., Washington D.C., American Psychiatric Association, 1994). However, these standards are conditioned by a decline in recognition functions which causes a severe disability in daily life or social life. Then, it is pointed out that the diagnosis is less than scientifically objective because the diagnosis may be influenced by the level of an individual's social life and further the specialty and experience of a physician who diagnoses particular conditions. In addition, definite diagnosis of Alzheimer's disease is conducted by pathohistological analyses and, in this respect, substantial inconsistency between clinical diagnosis and autopsy diagnosis exists.

At present, image diagnosis is employed as a supplemental means in clinical diagnosis of Alzheimer's diagnosis and it is possible to analyze brain functions, for example, decline of metabolism and atrophy in specific sites such as hippocampus, parietal lobe of cerebral cortex and the like which are specific for Alzheimer's disease by PET and SPECT. However, to define Alzheimer's disease based on lowering of a blood flow from parietal lobe to temporal lobe is very dangerous. In addition, there is a report showing that MRS test is useful for patients with dementia including those of Alzheimer's disease. Further, although CT-MRI image diagnosis is used, a lesion of white matter such as atrophy of brain, PVL or the like is not specific for Alzheimer type dementia. Since it has been reported that atrophy of brain proceeds with aging, the above observation is not necessarily found in Alzheimer type dementia. Furthermore, since an image obtained by MRI varies according to strength of a magnetic field, performance of the apparatus and imaging conditions, numerical data obtained in different facilities cannot he compared with each other except for atrophic change. In addition, there is a limit to image measurement. Further, enlargement of the ventricle can be recognized in vascular dementia cases and there are cases wherein atrophy of the hippocampus is observed after ischemia of the basilar artery.

Under these circumstances, many researchers have requested to develop biological diagnosis markers as a means for providing better precision and objectivity for clinical diagnosis of Alzheimer's disease. At the same time, the following important roles in the future will be expected.

1) Objective judgment system of effect of medicaments for treating Alzheimer's disease.

2) Detection of Alzheimer's disease before a diagnosis standard is met, or disease conditions are manifested.

Further, data obtained in different facilities can be compared with each other by using the same diagnosis marker. Therefore, development of biological diagnosis markers is recognized to be a most important field among fields of Alzheimer's disease studies and its future prospects will be expected. Approaches to development of biological diagnosis markers up to now are divided into those based on constitute components of characteristic pathological changes of Alzheimer's disease such as senile plaque and neurofibril change, and an approach based on other measures. Examples of the former include cerebrospinal fluid tau protein, Aβ and its precursor, βAPP. Examples of the latter include mydriasis test with cholilytic drug, Apo E and other genes relating to Alzheimer's disease. However, no good results have been obtained.

Serine proteases are also considered to play an important role in cancer cells. The reason why extermination of cancer by surgical treatment or topical irradiation of radioactive ray is difficult is the metastatic capability of cancer. To spread solid tumor cells in a body, they loosen their adhesion to original adjacent cells, followed by separating from original tissue, passing through other tissues to reach the blood vessels or lymph nodes, entering into the circulatory system through stratum basal and endothelial layer of the vessel, leave from the circulatory system at somewhere in the body, and surviving and proliferating in a new environment. While adhesion to adjacent epidermal cells is lost when expression of cadherin which is an intercellular adhesive molecule of epithelium is stopped, to break through tissues is considered to depend on proteolytic enzymes which decompose an extracellular matrix.

As enzymes which decompose the matrix, mainly, metal proteases (Rha, S. Y. et al., Breast Cancer Research Treatment, 43, 175, 1997) and serine proteases are known. They cooperate to decompose matrix proteins such as collagen, laminin and fibronectin. Among the serine proteases known to be concerned in decomposition of the matrix, in particular, there is urokinase type plasminogen activator (U-PA). U-PA has a role as a trigger specific for a protein decomposition chain reaction. Its direct target is plasminogen. It is present in blood abundantly and is a precursor of an inactive serine protease which accumulates in reconstructed sites of tissues such as injured sites and tumors as well as inflammatory sites. In addition, as proteases which are concerned in metastasis and infiltration of cancers, for example, a tissue factor, lysosomal type hydrolase and collagenase have been known.

At present, cancer is the top cause of death in Japan and more than 200,000 people die per year. Accordingly, specific substances which can be used as markers for diagnosis and therapy or prophylaxis of cancer are studied intensively. Such specific substances are referred to as tumor markers or tumor marker relating biomarkers. They are utilized in aid of diagnosis before treatment of cancer, for presuming carcinogenic organ and pathological tissue type, for monitoring effect of treatment, for finding recurrence early, for presuming prognosis, and the like. At present, tumor markers are essential in clinical analyses. Among them, alpha fetoprotein (AFP) which has high specificity to hepatocellular carcinoma and yolk sac tumor (Taketa K. et al., Tumour Biol., 9, 110, 1988), and carcinoembronic antigen (CEA) are used worldwide. In the future, tumor markers will be required more and more, and it is desired to develop, for example, organ specific markers and tumor cell specific markers which are highly reliable serologic diagnosis of cancer. Up to now, humunglandular kallikrein (hK2) which is a serine protease expressed at human prostatic epithelial cells has been reported as a marker for prostatic cancer. And, hK2 has 78% homology with the sequence of prostatic specific antigen (PSA) and PSA is also used widely as a biochemical marker of prostatic cancer (Mikolajczyk, S. d. et al., Prostate, 34, 44, 1998; Pannek, J. et al., Oncology, 11, 1273, 1997; Chu, T. M. et al., Tumour Biology, 18, 123, 1997; Hsieh, M. et al., Cancer Res., 57, 2651, 1997). Further, hK2 is reported to be useful as a marker for not only prostatic cancer but also stomach cancer (Cho, J. Y. et al. Cancer, 79, 878, 1997). Moreover, CYFRA (CYFRA 211) for measuring cytokeratin 19 fragment in serum is reported to be useful for lung cancer (Sugiyama, Y. et al., Japan J. Cancer Res., 85, 1178, 1994). Gastrin release peptide precursor (ProGRP) is reported to be useful as a tumor marker (Yamaguchi, K. et al., Japan, J. Cancer Res., 86, 698, 1995).

OBJECTS OF THE INVENTION

Thus, the main object of the present invention is to provide a novel serine protease which can be used for treating or diagnosing various diseases such as Alzheimer's disease (AD), epilepsy, cancer, inflammation, infertility, prostatomegaly and the like in various tissues such as v brain, lung, prostate, testicle, skeletal muscle, liver and the like, and can be used as an excellent marker instead of that presently used.

SUMMARY OF THE INVENTION

Under these circumstances, the present inventors have succeeded in cloning cDNA encoding novel human and mouse serine proteases.

In summary, the 1st feature of the present invention is the amino acid sequences of biologically active mature serine proteases BSSP2 and nucleotide sequences encoding the amino acid sequences.

That is, they are the amino acid sequence composed of 238 amino acids (mature type BSSP2 (SEQ ID NO: 2)) and a nucleotide sequence encoding the amino acid sequence (the 1st to 714th bases of SEQ ID NO: 1). In addition, they include amino acid sequences substantially similar to SEQ ID NO: 2 and nucleotide sequences encoding such similar amino acid sequences. Further, they include modified derivatives of proteins having these amino acid sequences. An amino acid sequence substantially similar to a given amino acid sequence used herein means an amino acid sequence derived from the given amino acid sequence by modification such as substitution, deletion, addition and/or insertion of one to several amino acids with maintaining the same property as that of the protein having the given amino acid sequence. The modified derivative of the proteins includes, for example, phosphate adduct, sugar chain adduct, metal adduct (e.g., calcium adduct), the protein fused to another protein such as albumin etc., dimer of the protein, and the like.

In the nucleotide sequences in the Sequence Listing hereinafter, the symbol "n" represents that any of the normal bases of a nucleic acid, i.e., adenine (a), cytosine (c), guanine (g) and thymine (t) is present at that position.

The 2nd feature of the present invention is an amino acid sequence composed of 273 amino acids [type 1 BSSP2 (SEQ ID NO: 4)] wherein 35 amino acids of −35th to −1st amino acids represented by SEQ ID NO: 4 are added to the N-terminus side of the mature BSSP2 amino acid sequence (SEQ ID NO: 2) and a nucleotide sequence encoding the amino acid sequence (247th to 1065th bases of SEQ ID NO: 3). In addition, this feature includes amino acid sequences substantially similar to SEQ ID NO: 4 and nucleotide sequences encoding these substantially similar amino acid sequences. Further, this feature includes modified derivatives of proteins having these amino acid sequences.

The 3rd feature of the present invention is an amino acid sequence composed of 311 amino acids (type 2 BSSP2 (SEQ ID NO: 6)] wherein 73 amino acids of −73rd to −1st amino acids represented by SEQ ID NO: 6 are added to the N-terminus side of the mature BSSP2 amino acid sequence (SEQ ID NO: 2) and a nucleotide sequence encoding the amino acid sequence (516th to 1448th bases of SEQ ID NO: 5). In addition, this feature includes amino acid sequences substantially similar to SEQ ID NO: 6 and nucleotide sequences encoding these substantially similar amino acid sequences. Further, this feature includes modified derivatives of proteins having there amino acid sequences.

The 4th feature of the present invention is an amino acid sequence composed of 445 amino acids [type 3 BSSP2 (SEQ ID NO: 8)] wherein 207 amino acids of −207th to −1st amino acids represented by SEQ ID NO: 8 are added to the N-terminus side of the mature BSSP2 amino acid sequence (SEQ ID NO: 2) and a nucleotide sequence encoding the amino acid sequence (116th to 1450th bases of SEQ ID NO: 7). In addition, this feature includes amino acid sequences substantially similar to SEQ ID NO: 8 and nucleotide sequences encoding these substantially similar amino acid sequences. Further, this feature includes modified derivatives of proteins having there amino acid sequences.

The 5th feature of the present invention is an amino acid sequence of a biologically active, mature human serine protease, hBSSP2, and a nucleotide sequence encoding the amino acid sequence. That is, they are an amino acid sequence [mature type hBSSP2 (SEQ ID NO: 10) composed of 240 amino acids represented by SEQ ID NO: 10 (1st to 240th amino acids) and a nucleotide sequence encoding the amino acid sequence (807th to 1526th bases of SEQ ID NO: 9). In addition, this feature includes amino acid sequences substantially similar to SEQ ID NO: 10 (1st to 240th amino acids) and nucleotide sequences encoding these substantially similar amino acid sequences. Further, this feature includes modified derivatives of proteins having there amino acid sequences.

The 6th feature of the present invention is an amino acid sequence composed of 457 amino acids (−217th to 240th amino acids of SEQ ID NO: 10) wherein 217 amino acids of −217th to −1st amino acids represented by SEQ ID NO: 10 are added to the N-terminus side of the mature human serine protease hBSSP2 amino acid sequence (1st to 240 amino acids of SEQ ID NO: 10) and a nucleotide sequence encoding the amino acid sequence (156th to 1526th bases of SEQ ID NO: 9). In addition, this feature includes amino acid sequences substantially similar to SEQ ID NO: 10 and nucleotide sequences encoding these substantially similar amino acid sequences. Further, this feature includes modified derivatives of proteins having there amino acid sequences.

The 7th feature of the present invention is an amino acid sequence composed of 217 amino acids of −217th to −1st amino acids of SEQ ID NO: 10 and a nucleotide sequence encoding the amino acid sequence (156th to 806th bases of SEQ ID NO: 9). In addition, this feature includes amino acid sequences substantially similar to the amino acid composed of 217 amino acids of −217th to −1st SEQ ID NO: 10 and nucleotide sequences encoding these substantially similar amino acid sequences. Further, this feature includes modified derivatives of proteins having there amino acid sequences.

The present invention also relates to the nucleotide sequences represented by SEQ ID NOS: 1, 3, 5, 7 and 9 as well as nucleotide sequences similar to them.

The 8th feature of the present invention is a vector comprising the nucleotide sequence according to any of the above 1st to the 7th feature, and transformant cells transformed with the vector.

The 9th feature of the present invention is a process for producing BSSP2 protein from the transformed cells of the 8th feature.

The 10th feature of the present invention is a transgenic non-human animal, wherein the expression level of BSSP2 gene has been altered.

The 11th feature of the present invention is an antibody against BSSP2 protein or its fragment and a process for producing thereof.

The 12th feature of the present invention is a method for determining BSSP2 protein or its fragment in a specimen using the antibody of the 11th feature.

The 13th feature is a diagnostic marker of diseases comprising BSSP2 protein.

Hereinafter, unless otherwise stated, the nucleotide sequence represented by each SEQ ID NO: includes the above-described various fragments thereof, and similar nucleotide sequences and their fragments. Likewise, the amino acid sequence represented by each SEQ ID NO: includes the above-described various fragments thereof, similar nucleotide sequences and their fragments, and modified derivatives thereof. In addition, unless otherwise stated, BSSP2, hBSSP2, and mBSSP2 include proteins having the above-described respective amino acid sequences.

DETAILED DESCRIPTION OF THE INVENTION

The nucleotide sequences encoding hBSSP2 or mBSSP2 of the present invention can be obtained by preparing mRNAs from cells expressing the protein and converting it into double stranded DNAs according to a conventional manner. For preparing mRNA, guanidine isothiocyanate-calcium chloride method (Chirwin, et al., Biochemistry, 18, 5294, 1979) or the like can be used. For preparing poly (A)+RNA from total RNAs, there can be used affinity chromatography using a carrier, for example, Sepharose, latex particles, etc., to which oligo (dT) is attached, and the like. The above-obtained RNA can be used as a template and treated with reverse transcriptase by using, as a primer, oligo (dT) which is complementary to the poly (A) strand at the 3'-terminus, or a random primer, or a synthesized oligo-nucleotide corresponding to a part of the amino acid sequence of hBSSP2 or mBSSP2 to obtain a hybrid MRNA strand comprising DNA or cDNA complementary to the MRNA. The double stranded DNA can be obtained by treating the above-obtained hybrid mRNA strand with *E. coli* RNase, *E. coli* DNA polymerase and *E. coli* DNA ligase to convert into a DNA strand.

It is also possible to carry out cloning by RT-PCR method using primers synthesized on the basis of the nucleotide sequence of hBSSP2 or mBSSP2 gene and using hBSSP2 or mBSSP2 expressing cell poly (A)+RNA as a template. Alternatively, the desired cDNA can be obtained without using PCR by preparing or synthesizing a probe on the basis of the nucleotide sequence of hBSSP2 or mBSSP2 gene and screening a cDNA library directly. Among genes obtained by these methods, the gene of the present invention can be selected by confirming a nucleotide sequence thereof. The gene of the present invention can also be prepared according to a conventional method using chemical syntheses of nucleic acids, for example, phosphoamidite method (Mattencci, M. D. et al., J. Am. Chem. Soc., 130, 3185, 1981) and the like.

By using the thus-obtained hBSSP2 or mBSSP2 gene, their expression in various tissues can be examined.

Figure 1:
FIG. 1 illustrates the results of northern blotting using mRNAs prepared from mice in Example 2 hereinafter.
Figure 2:
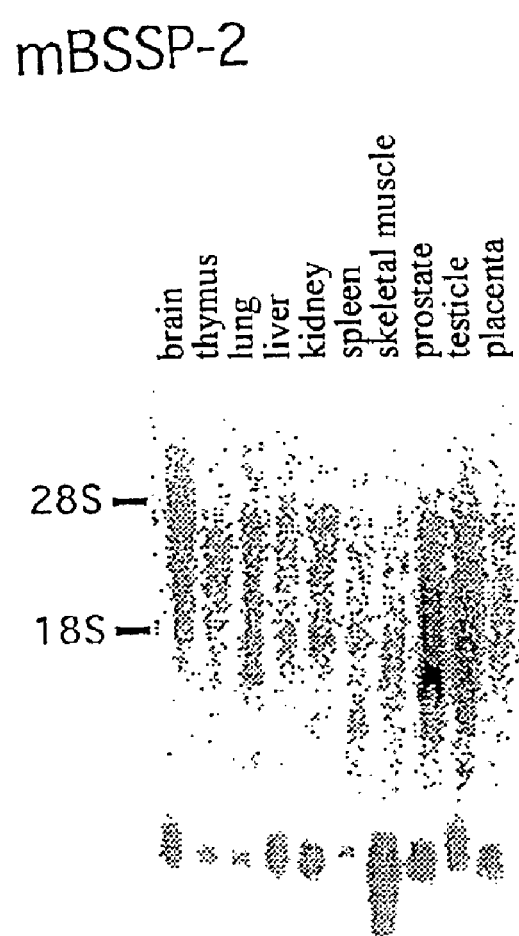
FIG. 2 illustrates the results of northern blotting using mRNAs prepared from mice in Example 2 hereinafter.
Figure 5:
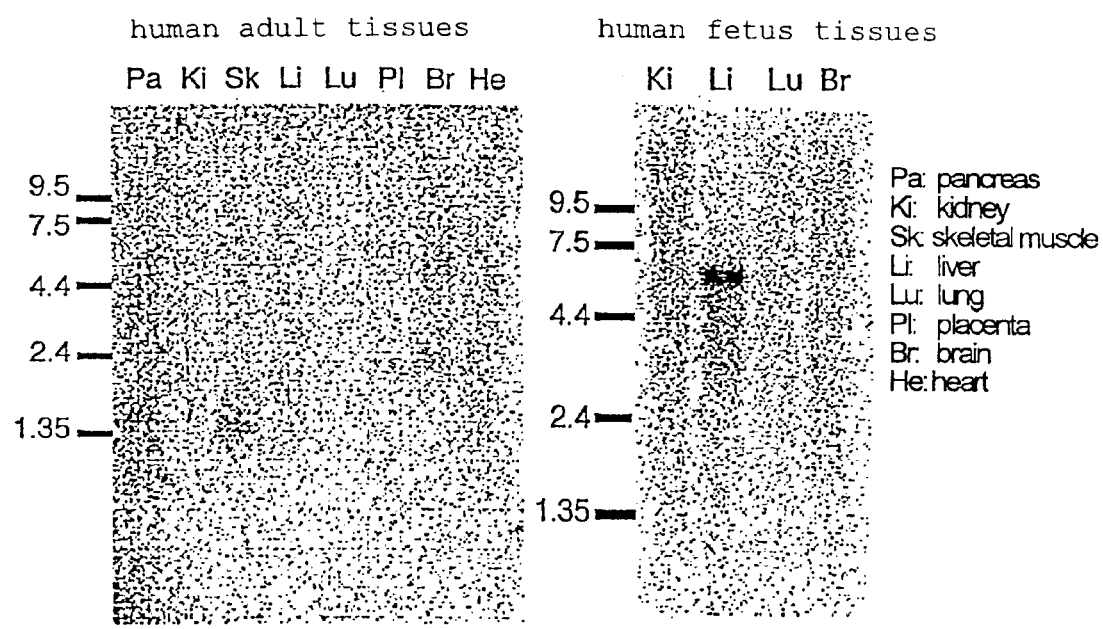
FIG. 5 illustrates the detection of hBSSP2 MRNA by northern hybridization.

In case of northern blotting analysis, mBSSP2 shows the expression in the head of a 15–20 days mouse fetus, and in the lung, prostate and testicle of a 3 month-old mouse. hBSSP2 shows the expression in brain, skeletal muscle and liver (see FIGS. 1, 2 and 5). In case of RT-PCR analysis, mBSSP2 shows the expression in the brain and testicle of a 12 day-old mouse, and hBSSP2 shows the expression in the braIn and skeletal muscle. Then, the novel proteases of the present invention are presumed to play various roles in the brain, prostate, lung, testicle, skeletal muscle and liver. For example, in the brain, there is a possibility that they can be used for treatment and diagnosis of brain diseases such as Alzheimer's disease (AD), epilepsy, brain tumor and the like. Further, in other tissues, there is a possibility that BSSP2 of the present invention and a gene encoding it can be used for treatment and diagnosis of various diseases such as cancer, inflammation, infertility, prostatomegaly and the like. Further, it is presumed they may have a certain influence on blood coagulation, fibrinolysis and complement systems. Furthermore, there is a possibility that inhibitors of serine proteases can be used for treatment and diagnosis of Alzheimer's disease, epilepsy, cancer, inflammation, infertility, prostatomegaly and the like.

The novel mouse serine protease can be divided into types 1, 2 and 3. It has been shown that type 1 is composed of 273 amino acids, type 2 is composed of 311 amino acids, and type 3 is composed of 445 amino acids. These amino acid sequences contain a common amino acid sequence of 238 amino acids whose N-terminus side starts with Ile-Val-Gly-Gly-Gln-Ala-Val (amino acid 1–7 of SEQ ID NO:2) as the mature serine protease. Further, the amino acid sequence of the mature serine protease contains a consensus sequence having serine protease activity. Since there are two or more amino acid sequences which are characteristic of sugar chain binding sites, the amino acid sequence is presumed to have at least two sugar chains.

Furthermore, in the novel human serine protease (hBSSP2), there are a transmembrane region and a scavenger receptor cysteine rich-like domain in the N-terminus side of hBSSP2 mature protein as seen from SEQ ID NO: 10.

The term "pro part" used herein means a part of a pro-form, i.e., the pro-form from which the corresponding active type protein part is removed. The term "pre part" used herein means a part of a prepro-form, i.e., the prepro-form from which the corresponding pro-form is removed. The term "prepro part" used herein means a part of a prepro-form, i.e., the prepro-form from which the corresponding active type protein part is removed.

The amino acid sequence represented by SEQ ID NO: 2 is the BSSP2 mature or active type protein composed of 238 amino acids, and the nucleotide sequence encoding the amino acid sequence represented by SEQ ID NO: 1 is composed of 714 bases. The present inventors have shown that the serine protease activity is maintained even when one to several amino acids of the N-terminus of the mature type protein of the present invention is deleted or added, while the sequence represented by SEQ ID NO: 2 is preferred.

The amino acid sequence represented by SEQ ID NO: 4 is type 1 BSSP2 protein composed of 273 amino acids, and the nucleotide sequence encoding the amino acid sequence represented SEQ ID NO: 3 is composed of 1685 bases. The sequence of the −35th to −1st amino acids is the prepro or pro part and the amino acid sequence represented by SEQ ID NO: 4 is considered to be a precursor type of the BSSP2 protein.

The amino acid sequence represented by SEQ ID NO: 6 is type 2 BSSP 2 protein composed of 311 amino acids and the nucleotide sequence encoding the amino acid sequence represented by SEQ ID NO: 5 is composed of 2068 bases. The sequence of the −73rd to −1st amino acids is the prepro or pro part and the amino acid sequence represented by SEQ ID NO: 6 is considered to be a precursor type of BSSP2 protein.

The amino acid sequence represented by SEQ ID NO: 8 is type 3 BSSP2 protein composed of 445 amino acids and the nucleotide sequence encoding the amino acid sequence represented by SEQ ID NO: 7 is composed of 2070 bases. The amino acid sequence of the −207th to −1st amino acids is the prepro or pro part and the amino acid sequence represented by SEQ ID NO: 8 is considered to be a precursor type of BSSP2 protein.

SEQ ID NOS: 4, 6 and 8 contain the common amino acid sequence represented by SEQ ID NO: 2 as the mature BSSP2 protein. Further, each of amino acid sequences of −25th to 238th amino acids in SEQ ID NOS: 4, 6 and 8 is the consensus sequence.

The amino acid sequence represented by SEQ ID NO: 10 is hBSSP2 protein composed of 457 amino acids and the nucleotide sequence encoding the amino acid sequence represented by SEQ ID NO: 9 is composed of 1371 bases. Since a transmembrane region and a scavenger receptor cysteine rich-like domain are present in the amino acid sequence of the −217th to −1st amino acids of SEQ ID NO: 10, it is considered that hBSSP2 exhibits its activity not only in the form of the mature protein but also in the form of an adduct of the −217th to −1st amino acids.

In general, many genes of eucaryotes exhibit polymorphism and, sometimes, one or more amino acids are substituted by this phenomenon. Further, even in such a case, sometimes, a protein maintains its activity. Then, the present invention includes a gene encoding a protein obtained by modifying a gene encoding any one of the amino acid sequences represented by SEQ ID NOS: 2, 4, 6, 8 and 10, artificially, in so far as the protein has the characteristic function of the gene of the present invention. Further, the present invention includes a protein which is a modification of any one of amino acid sequences represented by SEQ ID NOS: 2, 4, 6, 8 and 10 in so far as the protein has the characteristics of the present invention. Modification is understood to include substitution, deletion, addition and/or insertion. In particular, the present inventors have shown that, even when several amino acids are added to or deleted from the N-terminus amino acid of the BSSP2 mature protein represented by SEQ ID NO: 2, the resultant sequence maintains its activity.

That is, the present invention includes a protein comprising any one of the amino acid sequences described in SEQ ID NOS: 2, 4, 6, 8 and 10; an amino acid sequence encoded by any one of the nucleotide sequences represented by SEQ ID NOS: 1, 3, 5, 7 and 9; or one of these amino acid sequences wherein one to several amino acids have been substituted, deleted, added and/or inserted, and belonging to serine protease family.

Each codon for the desired amino acid itself has been known and can be selected freely. For example, codons can be determined according to a conventional manner by taking into consideration the frequency of use of codons in a host to be utilized (Grantham, R. et al., Nucleic Acids Res., 9, r43, 1989). Therefore, the present invention also includes a nucleotide sequence appropriately modified by taking into consideration the degeneracy of a codon. Further, these nucleotide sequences can be modified by a site directed mutagenesis using a primer composed of a synthetic oligonucleotide encoding the desired modification (Mark, D. F. et al., Proc. Natl. Acad. Sci. USA., 81, 5662, 1984), or the like.

Furthermore, the DNA of the present invention includes DNA which is hybridizable to any one of the nucleotide sequences described in SEQ ID NOS: 1, 3, 5, 7 and 9 or nucleotide sequences complementary to these nucleotide sequences in so far as the protein encoded by the nucleotide sequence has the same properties as those of the BSSP2 of the present invention. It is considered that many of the sequences which are hybridizable to a given sequence under stringent conditions have a similar activity to that of a protein encoded by the given sequence. The stringent conditions according to the present invention includes, for example, incubation in a solution containing 5×SSC, 5% Denhardt's solution (0.1% BSA, 0.1% Ficol 1400, 0.1% PVP), 0.5% SDS and 20 µg/ml denatured salmon sperm DNA at 37° C. overnight, followed by washing with 2×SSC containing 0.1% SDS at room temperature. Instead of SSC, SSPE can be appropriately used.

Probes for detecting a BSSP2 gene can be designed based on any one of nucleotide sequences described in SEQ ID NOS: 1, 3, 5, 7 and 9. Or, primers can be designed for amplifying DNA or RNA containing the nucleotide sequence. To design probes or primers is carried out routinely by a person skilled in the art. An oligonucleotide having a designed nucleotide sequence can be synthesized chemically. And, when a suitable label is added to the oligonucleotide, the resultant oligonucleotide can be utilized in various hybridization assay. Or, it can be utilized in nucleic acid synthesis reactions such as PCR. An oligonucleotide to be utilized as a primer has, preferably, at least 10 bases, more preferably 15 to 50 bases in length. An oligonucleotide to be utilized as a probe has, preferably, 100 bases to full length.

Moreover, it is possible to obtain a promoter region and an enhancer region of a BSSP2 gene present in the genome based on the CDNA nucleotide sequence of BSSP2 provided by the present invention. Specifically, these control regions can be obtained according to the same manner as described in JP 6-181767 A; J. Immunol., 155, 2477, 1995; Proc. Natl. Acad. Sci., USA, 92, 3561, 1995 and the like. The promoter region used herein means a DNA region which is present upstream from a transcription initiation site and controls expression of a gene. The enhancer region used herein means a DNA region which is present in an intron, a 5'-non-translated region or a 3'-non-translated region and enhances expression of a gene.

The present invention also relates to a vector comprising the nucleotide sequence represented by SEQ ID NO: 1 or a nucleotide sequence encoding the amino acid sequence represented by SEQ ID NO: 2; the nucleotide sequence represented by SEQ ID NO: 3 or a nucleotide sequence encoding the amino acid sequence represented by SEQ ID NO: 4; the nucleotide sequence represented by SEQ ID NO: 5 or a nucleotide sequence encoding the amino acid sequence represented by SEQ ID NO: 6; the nucleotide sequence represented by SEQ ID NO: 7 or a nucleotide sequence encoding the amino acid sequence represented by SEQ ID NO: 8; or the nucleotide sequence represented by SEQ ID NO: 9 or a nucleotide sequence encoding the amino acid sequence represented by SEQ ID NO: 10; or a nucleotide sequence similar to them. A nucleotide sequence similar to a given nucleotide sequence used herein means a nucleotide sequence which is hybridizable to the given nucleotide sequence or its complementary nucleotide sequence under the above-described stringent conditions and which encodes a protein having the same properties as those of the protein encoded by the nucleotide sequence.

The vector is not specifically limited in so far as it can express the protein of the present invention. Examples thereof include pBAD/His, pRSETA, pcDNA2.1, pTrcHis2A, pYES2, pBlueBac4.5, pcDNA3.1 and pSec-Tag2 manufacture by Invitrogen, pET and PBAC manufactured by Novagen, pGEM manufactured by Promega, pBluescriptII manufactured by Stratagene, pGEX and pUC18/19 manufactured by Pharmacia, PfastBAC1 manufactured by GIBCO and the like. Preferably, a protein expression vector (described in the specification of a patent application entitled "Protein expression vector and its use" and filed by the same applicant on the same day) is used. This expression vector is constructed by using pCRII-TOPO vector described in the Examples hereinafter, or a commercially available expression vector, for example pSecTag2A vector or pSecTag2B vector (Invitrogen) and integrating a secretory signal nucleotide sequence suitable for expression of the protein of the present invention, in the 3' downstream side thereof, a Tag nucleotide sequence, a cleavable nucleotide sequence and a cloning site, into which a nucleotide sequence encoding a target protein can be inserted, in this order. More specifically, it is preferred to use trypsin signal as the secretory signal, a nucleotide sequence encoding polyhistidine as the Tag nucleotide sequence, and a nucleotide sequence encoding an amino acid sequence which is susceptible to enzyme-specific cleavage, i.e., a nucleotide sequence encoding the amino acid sequence of Asp-Asp-Asp-Asp-Lys SEQ ID NO:42 (said amino acid sequence is recognized by enterokinase, and the recombinant fusion protein is cleaved at the C-terminus part thereof) as the cleavable nucleotide sequence.

Furthermore, the present invention provides transformed cells having the nucleotide sequence of the present invention in an expressible state by means of the above vector. Preferably, host cells to be used for the transformed cells of the present invention are animal cells and insect cells. However, host cells include any cells (including those of microorganisms) which can express a nucleotide sequence encoding the desired protein in the expression vector of the present invention and can secrete extracellularly.

The animal cells and insect cells used herein include cells derived from human beings and cells derived from flies or silk worms. For example there are CHO cells, COS cells, BHK cells, Vero cells, myeloma cells, HEK293 cells, HeLa cells, Jurkat cells, mouse L cells, mouse C127 cells, 10 mouse FM3A cells, mouse fibroblast, osteablast, cartilage cells, S2, Sf9, Sf21, High Five™ (registered trade mark) cells and the like.

The protein of the present invention as such can be expressed as a recombinant fused protein so as to facilitate isolation, purification and recognition. The recombinant fused protein used herein means a protein expressed as an adduct wherein a suitable peptide chain is added to the N-terminus and/or C-terminus of the desired protein expressed by a nucleotide sequence encoding the desired protein. The recombinant protein used herein means that obtained by integrating a nucleotide sequence encoding the desired protein in the expression vector of the present invention and cut off an amino acid sequence which derived from nucleic acids other than those encoding the desired protein from the expressed recombinant fused protein, and is substantially the same as the protein of the present invention.

Introduction of the above vector into host cells can be carried out by, for example, transfection according to the lipopolyamine method, DEAE-dextran method, Hanahan method, lipofectin method or calcium phosphate method, microinjection, eletroporation and the like.

As described above, the present invention also relates to a process for producing hBSSP2 of mBSSP2 comprising culturing cells transformed with the above nucleotide sequence of the present invention and collecting the produced hBSSP2 of mBSSP2. The culture of cells and separation and purification of the protein can be carried out by a per se known method.

The present invention also relates to an inhibitor of the novel serine protease of the present invention. Screening of the inhibitor can be carried out according to a per se known method such as comparing the enzyme activity upon bringing into contact with a candidate compound with that without contact with the candidate compound, or the like The present invention relates to a non-human transgenic animal whose expression level of hBSSP2 or mBSSP2 gene has been altered. The hBSSP2 or mBSSP2 gene used herein includes cDNA, genomic DNA or synthetic DNA encoding hBSSP2 or mBSSP2. In addition, expression of a gene includes any steps of transcription and translation. The non-human transgenic animal of the present invention is useful for studies of functions or expression control of hBSSP2 or mBSSP2, elucidation of mechanisms of diseases in which hBSSP2 or mBSSP2 is presumed to be involved, and development of disease model animals for screening and safety test of medicine.

In the present invention, expression of a gene can be modified artificially by mutagenizing at a part of several important sites which control normal gene expression (enhancer, promoter, intron, etc.) such as deletion, substitution, addition and/or insertion to increase or decrease an expression level of the gene in comparison with its inherent expression level. This mutagenesis can be carried out according to a known method to obtain the transgenic animal.

In a narrow sense, the transgenic animal means an animal wherein a foreign gene is artificially introduced into reproductive cells by gene recombinant techniques. In a broad sense, the transgenic animal includes an antisense transgenic animal the function of whose specific gene is inhibited by using antisense RNA, an animal whose specific gene is knocked out by using embryonic stem cells (ES cells), and an animal into which point mutation DNA is introduced, and the transgenic animal means an animal into which a foreign gene is stably introduced into a chromosome at an initial stage of ontogeny and the genetic character can be transmitted to the progeny.

The transgenic animal used herein should be understood in a broad sense and includes any vertebrates other than a human being. The transgenic animal of the present invention is useful for studies of functions or expression control of BSSP2, elucidation of mechanisms of diseases associated with cells expressing in a human being, and development of disease model animals for screening and safety test of medicine.

As a technique for creating the transgenic animal, a gene is introduced into a nucleus in a pronucleus stage of egg cells with a micropipette directly under a phase-contrast microscope (microinjection, U.S. Pat. No. 4,873,191). Further, there are a method using embryonic stem cell (ES cell), and the like. In addition, there are newly developed methods such as a method wherein a gene is introduced into a retroviral vector or adenoviral vector to infect egg cells, a sperm vector method wherein a gene is introduced into egg cells through sperms, and the like.

A sperm vector method is a gene recombinant technique wherein a foreign gene is incorporated into sperm cells by adhesion, electroporation, etc., followed by fertilization of egg cells to introduce the foreign gene into the egg cells (M. Lavitranoet et al., Cell, 57, 717, 1989). Alternatively, an in vivo site specific gene recombinant technique such as that using cre/loxP recombinase system of bacteriophage P1, FLP recombinase system of *Saccharomyces cerevisiae*, etc. can be used. Furthermore, introduction of a transgene of the desired protein into a non-human animal using a retroviral vector has been reported.

For example, a method for creating a transgenic animal by microinjection can be carried out as follows.

First, a transgene primarily composed of a promoter responsible for expression control, a gene encoding a specific protein and a poly A signal is required. It is necessary to confirm expression modes and amounts between respective systems because an expression mode and amount of a specific molecule is influenced by a promoter activity, and transgenic animals differ from each other according to a particular system due to the difference in a copy number of an introduced transgene and a introduction site on a chromosome. An intron sequence which is spliced may be previously introduced before the poly A signal because it has been found that an expression amount varies due to a non-translation region and splicing. Purity of a gene to be used for introduction into fertilized egg cells should be as high as possible. This is of importance. Animals to be used include a mouse for collecting fertilized eggs (5 to 6 week old), a male mouse for mating, a false pregnancy female mouse, a seminiferous tubule-ligated mouse, and the like.

For obtaining fertilized egg cells efficiently, ovulation may be induced with gonadotropin or the like. Fertilized egg cells are recovered and a gene in an injection pipette is injected into male pronucleus of the egg cells by microinjection. For returning the injected egg cells to a fallopian tube, an animal (false pregnancy female mouse, etc.) is provided and about 10 to 15 eggs/mice are transplanted. Then, genomic DNA is extracted from the end part of the tail to confirm whether the transgene is introduced into newborn mouse or not. This confirmation can be carried out by detection of the transgene with southern blot technique or PCR technique, or by positive cloning wherein a marker gene, which is activated only when homologous recombination is caused, has been introduced. Further, transcribed products derived from the transgene are detected by northern blot technique or RT-PCR technique to confirm expression of the transgene. Or, western blotting can be carried out with a specific antibody to a protein.

The knockout mouse of the present invention is treated so that the function of mBSSP2 gene is lost. A knockout mouse means a transgenic mouse in which any one of its genes is destroyed by homologous recombination technique so that its function is deficient. A knockout mouse can be created by carrying out homologous recombination with ES cells and selecting embryonic stem cells wherein either of allele genes are modified or destroyed. For example, embryonic stem cells whose genes are manipulated at the blastocyte or morula stage of fertilized eggs are injected to obtain a chimeric mouse wherein cells derived from the embryonic stem cells are mixed with those derived from the embryo. The chimeric mouse (chimeric means a single individual formed by somatic cells based on two or more fertilized eggs) can be mated with a normal mouse to create a heterozygote mouse wherein all of the allele genes have been modified or destroyed. Further, a homozygote mouse can be created by mating heterozygote mice.

Homologous recombination means recombination between two genes whose nucleotide sequences are the same or very similar to each other in terms of gene recombination mechanism. PCR can be employed to select homologous recombinant cells. A PCR reaction can be carried out by using a part of a gene to be inserted and a part of a region where the insertion is expected as primers to find out occurrence of homologous recombination in cells which give an amplification product. Further, for causing homologous recombination in a gene expressed in embryonic stem cells, homologous recombinant cells can readily be selected by using a known method or its modification. For example, cells can be selected by joining a neomycin resistant gene to a gene to be introduced to impart neomycin resistance to cells after introduction.

The present invention also provide an antibody recognizing hBSSP2 or mBSSP2 or a fragment thereof. The antibody of the present invention includes an antibody against a protein having the amino acid sequence described in any of SEQ ID NOS: 2, 4, 6, 8 and 10 or its fragment. An antibody against hBSSP2 or mBSSP2 or a fragment thereof (e.g., polyclonal antibody, monoclonal antibody, peptide antibody) or an antiserum can be produced by using hBSSP2 or mBSSP22 or a fragment thereof, etc. as an antigen according to a per se known process for producing an antibody or an antiserum.

The hBSSP2 or mBSSP2 of a fragment thereof is administered to a site of a warm-blooded animal where an antibody can be produced by administration thereof as such or together with a diluent or carrier. For enhancing the antibody production, upon administration, Freund's complete adjuvant or Freund's incomplete adjuvant may be administered. Normally, the administration is carried out once every 1 to 6 weeks, 2 to 10 times in all. Examples of the warm-blooded to be used include monkey, rabbit, dog, guinea pig, mouse, rat, sheep, goat, chicken and the like with mouse and rat being preferred. As rats, for example, Wistar and SD rats are preferred. As mice, for example, BALB/c, C57BL/6 and ICR mice are preferred.

For producing monoclonal antibody producer cells, individuals whose antibody titer have been recognized are selected from warm-blooded animals, e.g., a mouse immunized with an antigen. Two to 5 days after the last immunization, the spleen or lymph node of the immunized animal is collected and antibody producer cells contained therein are subjected to cell fusion with myeloma cells to prepare a monoclonal antibody producer hybridoma. The antibody titer in an antiserum can be determined by, for example, reacting the antiserum with a labeled hBSSP2 or mBSSP2 as described hereinafter, followed by measurement of the activity bound to the antibody. The cell fusion can be carried out according to a known method, for example, that described by Koehler and Milstein (Nature, 256, 495, 1975) or its modifications (J. Immunol. Method, 39, 285, 1980; Eur. J. biochem, 118, 437, 1981; Nature, 285, 446, 1980). As a fusion promoting agent, there are polyethylene glycol (PEG), Sendai virus and the like. Preferably, PEG is used. Further, for improving fusion efficiency, lectin, poly-L-lysine or DMSO can be appropriately added.

Examples of myeloma cells include X-63Ag8, NS-1, P3U1, SP2/0, AP-1 and the like with SP2/0 being preferred. The preferred ratio of the number of the antibody producer cells (spleen cells): the number of spleen cells are 1:20 to 20:1. PEG (preferably PEG 1000 to PEG 6000) is added at a concentration of about 10 to 80% and the mixture is incubated at 20 to 40° C., preferably 30 to 37° C. for 1 to 10 minutes to carry out the cell fusion efficiently. Screening of anti-hBSSP2 or mBSSP2 antibody producer hybridomas can be carried out by various methods. For example, a supernatant of a hybridoma culture is added to a solid phase to which hBSSP2 or mBSSP2 antigen is adsorbed directly or together with a carrier (e.g., microplate), followed by addition of an anti-immunoglobulin antibody (in case that the cells used in cell fusion are those of a mouse, anti-mouse immunoglobulin antibody is used) or protein A to detect the anti-hBSSP2 or mBSSP2 monoclonal antibody attached to the solid phase. Or, a supernatant of a hybridoma culture is added to a solid phase to which an anti-immunoglobulin antibody or protein A is adsorbed, followed by addition of hBSSP2 or mBSSP2 labeled with a radioactive substance, an enzyme, etc., to detect the anti-hBSSP2 or mBSSP2 monoclonal antibody attached to the solid phase.

Selection and cloning of the anti-hBSSP or mBSSP monoclonal antibody can be carried out according to a per se known method or its modification. Normally, a HAT (hypoxanthine, aminopterin, thymidine)-added medium for culturing animal cells is used. Any culture medium can be used for selection, cloning and growing up in so far as the hybridoma can grow. For example, there can be used RPMI culture medium containing 1 to 20%, preferably 10 to 20% fetal bovine serum, a serum-free medium for culturing hybridomas. Preferably, the culture is carried out at a temperature of about 37° C. Normally, the culture time is 5 days to 3 weeks, preferably 1 week to 2 weeks. Normally, the culture is carried out under 5% $CO_2$. The antibody titer of a supernatant of a hybridoma culture can be measured according to the same manner as that of the above-described measurement of anti-BSSP2 antibody titer in an antiserum. That is, examples of the measurement to be used include radioimmunoassay (RIA), enzyme-linked immunosorbent assay (ELISA), FIA (fluorescence immunoassay), plaque assay, agglutination reaction method, and the like. Among them, ELISA as shown below is preferred.

Screening by ELISA

A protein prepared according to the same operation as that for an immunogen is immobilized on the surface of each well of an ELISA plate. Next, BSA, MSA, OVA, KLH, gelatin, skimmed milk, or the like is immobilized on each well to prevent non-specific adsorption. A supernatant of a hybridoma culture is added to each well and is allowed to stand for a given time so that an immunological reaction proceeds. Each well is washed with a washing solution such as PBS or the like. Preferably, a surfactant is added to this washing solution. An enzyme labeled secondary antibody is added and allowed to stand for a given time. As the enzyme to be used for the label, there can be used β-galactosidase, alkaline phosphatase, peroxidase and the like. After washing each well with the same washing solution, a substrate solution of the labeled enzyme used is added so that an enzymatic reaction proceeds. When the desired antibody is present in the supernatant of a hybridoma culture, the enzymatic reaction proceeds and the color of the substrate solution is changed.

Normally, cloning is carried out by a per se known method such as semi-solid agar method, limiting dilution method and the like. Specifically, after confirming a well in which the desired antibody is produced by the above-described method, cloning is carried out to obtain a single clone. For cloning, it is preferred to employ limiting dilution method wherein hybridoma cells are diluted so that one colony is formed per one well of a culture plate. For cloning by limiting dilution method, feeder cells can be used, or a cell growth factor such as interleukin 6, etc. can be added to improve colony forming capability. In addition, cloning can be carried out by using FACS and single cell manipulation method. The cloned hybridoma is preferably cultured in a serum-free culture medium and an optimal amount of an antibody is added to its supernatant. The single hybridoma thus obtained can be cultured in a large amount by using a flask or a cell culture device, or cultured in the abdominal cavity of an animal (J. Immunol. Meth., 53, 313, 1982) to obtain a monoclonal antibody. When culturing in a flask, there can be used a cell culture medium (e.g., IMDM, DMEM, RPMI1640, etc.) containing 0 to 20% of FCS. When culturing in the abdominal cavity of an animal, the animal to be used is preferably the same species or the same line as that from which the myeloma cells used in the cell fusion are derived, a thymus deficient nude mouse or the like, and the hybridoma is transplanted after administration of a mineral oil such as pristane, etc. After 1 to 2 weeks, myeloma cells are proliferated in the abdominal cavity to obtain ascites containing a monoclonal antibody.

The monoclonal antibody of the present invention which does not cross-react with other proteins can be obtained by selecting a monoclonal antibody which recognizes an epitope specific to hBSSP2 or mBSSP2. In general, an epitope presented by an amino acid sequence composed of at least 3, preferably 7 to 20 successive amino acid residues in an amino acid sequence which constitutes a particular protein is said to be an inherent epitope of the protein. Then, a monoclonal antibody recognizing an epitope constituted by a peptide having an amino acid sequence composed of at least 3 successive amino acid residue selected from the amino acid residues disclosed in any of SEQ ID NOS: 2, 4, 6 and 8 can be said to be the monoclonal antibody specific for BSSP2 of the present invention. An epitope common to BSSP2 family can be selected by selecting an amino acid sequence conservative among the amino acid sequences described in SEQ ID NOS: 2, 4, 6, 8 and 10. Or, in case of a region containing an amino acid sequence specific for each sequence, a monoclonal antibody which can differentiate respective proteins can be selected.

Separation and purification of the anti-hBSSP2 or mBSSP2 monoclonal antibody, like a conventional polyclonal antibody, can be carried out according to the same manner as those of immunoglobulins. As a known purification method, there can be used a technique, for example, salting out, alcohol precipitation, isoelectric precipitation, electrophoresis, ammonium sulfate precipitation, absorption and desorption with an ion exchange material (e.g., DEAE), ultrafiltration, gel filtration, or specific purification by collecting only an antibody with an antibody-binding solid phase or an active adsorber such as protein A or protein G, etc., and dissociating the binding to obtain the antibody. For preventing formation of aggregates during purification or decrease in the antibody titer, for example, human serum albumin is added at a concentration of 0.05 to 2%. Alternatively, amino acids such as glycine, α-alanine, etc., in particular, basic amino acids such as lysine, arginine, histidine, etc., saccharides such as glucose, mannitol, etc., or salts such as sodium chloride, etc. can be added. In case of IgM antibody, since it is very liable to be aggregated, it may be treated with β-propionilactone and acetic anhydride.

The polyclonal antibody of the present invention can be produced according to a per se known method or its modification. For example, an immunogen (protein antigen) per se or a complex thereof with a carrier protein is prepared and, according to the same manner as that in the above monoclonal antibody production, a warm-blooded animal is immunized. A material containing an antibody against the protein of the present invention or its fragment is collected from the immunized animal and the antibody is separated and purified to obtain the desired antibody. As for a complex of an immunogen and a carrier protein for immunizing a warm-blooded animal, the kind of a carrier protein and the mixing ratio of a carrier and a hapten are not specifically limited in so far as an antibody against hapten immunized by cross-linking with the carrier is efficiently produced. For example, there can be used about 0.1 to 20, preferably about 1 to 5 parts by weight of bovine serum albumin, bovine cycloglobulin, hemocyanin, etc. coupled with one part by weight of a hapten. For coupling a carrier and a hapten, various condensing agents can be used. Examples thereof include glutaraldehyde, carbodiimide or maleimide active ester, active ester agents having thiol group or dithiopyridyl group, and the like. The condensed product is administered as such or together with a carrier or diluent to a site of a warm-blooded animal where an antibody can be produced. For enhancing the antibody production, upon administration, Freund's complete adjuvant or Freund's incomplete adjuvant may be administered. Normally, the administration is carried out once every 2 to 6 weeks, 3 to 10 times in all. The polyclonal antibody can be collected from blood, ascites, or the like, preferably blood of the immunized animal. The polyclonal antibody titer in an antiserum can be measured according to the same manner as measurement of the above monoclonal antibody titer in the antiserum. Separation and purification of the polyclonal antibody, like the above monoclonal antibody, can be carried out according to the same manner as those of immunoglobulins.

The monoclonal antibody and polyclonal antibody against hBSSP2 or mBSSP2 or a fragment thereof can be utilized for diagnosis and treatment of diseases associated with cells expressing hBSSP2 or mBSSP2. By using these antibodies, hBSSP2 or mBSSP2 or a fragment thereof can be determined based on their immunological binding to hBSSP2 or mBSSP2 or a fragment thereof of the present invention. Specifically, examples of a method for determining hBSSP2 or mBSSP2 or a fragment thereof in a specimen by using these antibodies include a sandwich method wherein the antibody attached to an insoluble carrier and the labeled antibody are reacted with hBSSP2 or mBSSP2 or a fragment thereof to form a sandwich complex and the sandwich complex is detected, as well as a competitive method wherein labeled hBSSP2 or mBSSP2, and hBSSP2 or mBSSP2 or a fragment thereof in the specimen are competitively reacted with the antibody and hBSSP2 or mBSSP2 or a fragment thereof in the specimen is determined based on the amount of the labeled antigen reacted with the antibody.

As a sandwich method for determining hBSSP2 or mBSSP2 or a fragment thereof, there can be used a two step method, a one step method and the like. In the two step method, first, the immobilized antibody is reacted with hBSSP2 or mBSSP2 or a fragment thereof and then unreacted materials are completely removed by washing, followed by addition of the labeled antibody to form immobilized antibody-hBSSP2 or mBSSP2-labeled antibody. In the one step method, the immobilized antibody, labeled antibody and hBSSP2 or mBSSP2 or a fragment thereof are added at the same time.

Examples of an insoluble carrier used for the determination include synthetic resins such as polystyrene, polyethylene, polypropylene, polyvinyl chloride, polyester, polyacrylate, nylon, polyacetal, fluorine plastic, etc.; polysaccharides such as cellulose, agarose, etc.; glass; metal; and the like. An insoluble carrier may be shaped in various forms, for example, tray, sphere, fiber, rod plate, container, cell, test tube, and the like. The antibody adsorbed by a carrier is stored at a cold place in the presence of an appropriate preservative such as sodium azide or the like.

For immobilization of the antibody, a known chemical bonding method or a physical adsorption can be used. Examples of a chemical bonding method include a method using glutaraldehyde; maleimide method using N-succinimidyl-4-(N-maleimidomethyl)cyclohexane-1-carboxylate, N-succinimdyl-2-maleimide acetate or the like; carbodiimide method using 1-ethyl-3-(3-dimethylaminopropyl) carbodiimide hydrochloride; or the like. In addition, there are maleimidobenzoyl-N-hydroxysuccinimide ester method, N-succinimidyl-3-(2-pyridylthio)propionic acid method, bisdiazobenzidine method, and dipalmityllysine method. Or, it is possible to capture a complex formed beforehand by reacting a material to be tested with two antibodies, whose epitopes are different, with an immobilized a 3rd antibody against the antibody.

For labeling, it is preferred to use an enzyme, fluorescent substance, luminous substance, radioactive substance, metal chelate, or the like. Examples of the enzyme include peroxidase, alkaline phosphatase, β-D-galactosidase, malate dehydrogenase, *Staphylococcus* nuclease, δ-5-steroidisomerase, α-glycerol phosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholinesterase and the like. Examples of the fluorescent substance include fluorescein isothiocyanate, phycobiliprotein, rhodamine, phycoerythrin, phvcocyanin, allophycocyanin, o-phthalaldehyde, and the like. Examples of the luminous substance include isoluminol, lucigenin, luminol, aromatic acridinium ester, imidazole, acrdinium salt and its modified ester, luciferin, luciferase, aequorin and the like. Examples of the radioactive substance include $^{125}I$, $^{127}I$, $^{131}I$, $^{14}C$, $^{3}H$, $^{32}P$, $^{35}S$ and the like. The labeling material is not limited to them and any material which can be used for immunological determination can be used. Further, a low molecular weight hapten such as biotin, dinitrophenyl, pyridoxal or fluorescamine may be attached to the antibody. Preferably, horseradish peroxidase is used as a labeling enzyme. This enzyme can be reacted with various substrates and can readily be attached to the antibody by periodate method.

When an enzyme is used as a labeling material, a substrate and, if necessary, a coloring enzyme is used for measuring its activity. In case of using peroxidase as the enzyme, $H_2O_2$ is used as a substrate and, as a coloring agent, there can be used 2,2'-azino-di-[3-ethylbenzthiazoline sulfonic acid] ammonium salt (ABTS), 5'-amincsalicylic acid, o-phenylenediamine, 4-aminoantipyrine, 3,3',5,5'-tetramethylbenzidine and the like. In case of using alkaline phosphatase as the enzyme, o-nitrophenylphosphate, p-nitrophenylphosphoric acid, or the like can be used as a substrate. In case of using β-D-galactosidase as the enzyme, fluorescein-d-(β-D-galactopyranoside), 4-methylumbelliphenyl-β-D-galactopyranoside, or the like can be used as a substrate. The present invention also includes a kit comprising the above monoclonal antibody, polyclonal antibody and reagents.

As a cross-linking agent, a known cross-linking agent such as N,N'-o-phenylenedimaleimide, 4-(N-maleimidomethyl)cyclohexanoate-N-succinimide ester, 6-maleimidohexanoate-N-succineimide ester, 4,4'-dithiopyridine or the like can be utilized. The reaction of these cross-linking agents with enzymes and antibodies can be carried out by a known method according to properties of a particular cross-linking agent. Further, as the antibody, a fragment thereof, for example, Fab', Fab, F(b'2) can be used as the case may be. A labeled enzyme can be obtained by the same treatment regardless of whether the antibody is polyclonal or monoclonal. When the above labeled enzyme obtained by using a cross-linking agent is purified by a known method such as affinity chromatography or the like, an immunoassay system having more higher sensitivity can be obtained. The enzyme labeled and purified antibody is stored in a dark cold place with addition of a stabilizer such as thimerosal, glycerin or after lyophilization.

An objective to be determined is not specifically limited in so far as it is a sample containing BSSP2 or a fragment thereof, or a sample containing a precursor of BSSP2 or a fragment thereof and includes body fluids such as plasma, serum, blood, serum, urine, tissue fluid, cerebrospinal fluid and the like.

The following Examples further illustrate the present invention in detail but are not construed to limit the scope thereof.

EXAMPLE 1

Cloning of Novel Serine Protease mBSSP2 Gene

The cloning was carried out by PCR using a mouse brain cDNA library (Clontech) as a template and nucleotide sequences corresponding to an amino acid sequence common to serine proteases represented by Primer 1: GTG CTC ACN GCN GCB CAY TG (SEQ ID NO: 20)

Primer 2: CCV CTR WSD CCN CCN GGC GA (SEQ ID NO: 21)

as primers. Namely, 5 μl of the template, 5 μl of 10×ExTaq buffer, 5 μl of dNTP, 10 pmol of each of the above primers and 0.5 μl of ExTaq (TAKARA) were added and the total volume was adjusted to 50 μl with sterilized water. PCR was carried out by repeating a cycle of heating at 94° C. for 0.5 minute, at 55° C. for 0.5 minute and then at 72° C. for 1 minute, 30 times. The PCR product was mixed with pCR II-TOPO vector attached to TOPO TA cloning kit (Invitrogen) and the mixture was allowed to stand at room temperature for 5 minutes. Then, according to a conventional manner, E. coli Top 10 attached to the kit was transformed and applied to a LB (Amp+) plate (containing 100 μg/ml of ampicillin). According to a conventional manner, a plasmid was extracted from each colony obtained and its nucleotide sequence was determined by cycle sequencing method with a fluorescence sequencer (ABI). Homology of the sequence of each clone was examined by means of GenBank. Regarding an unknown sequence, i.e., BSSP2 gene, the full length cDNA was obtained by 5' RACE and 3' RACE and, according to the same manner as described above, the nucleotide sequence was determined. Namely, BSSP2 clone specific primers, GSP1 primers [mBSSP2.2 (SEQ ID NO: 27) or mBSSP2.0 (SEQ ID NO: 22)] and GSP2 primers [mBSSP2R2 (SEQ ID NO: 28) or mBSSP2.1 (SEQ ID NO: 23)] were prepared. PCR was carried out by using mouse brain Marathon-Ready cDNA (Clontech), AP1 primer attached to this reagent and either of the above GSP1 primers and heating at 94° C. for 2 minutes once and repeating a cycle of heating at 94° C. for 30 seconds, at 60° C. for 30 seconds and then at 72° C. for 30 seconds 35 times. Then, 5 μl of the PCR product diluted to 1/100, 5 μl of 10x buffer, 5 μl of dNTP, 10 pmol of either of 10 μM of the above GSP2 primer, 10 pmol of AP2 primer attached to the above reagent and 0.5 unit of ExTaq were admixed and adjusted to 50 μl with sterilized water. Then, according to the same manner as the above, PCR was carried out. The PCR product was cloned by the above TOPO TA cloning kit and sequenced to obtain the upstream and downstream regions of the above clone. At this time, as for a clone which seemed not to cover the full length of a protein, the specific primers shown hereinafter were prepared based on the newly found nucleotide sequence. Further, based on this sequence, the primers capable of amplifying ORF as shown hereinafter [mBSSPF7 (SEQ ID NO: 26), mBSSP2R/E (SEQ ID NO: 29)] were prepared and PCR carried out using mouse brain Marathon-ready cDNA as a template to confirm that these clones were identical. This was cloned into pCR II-TOPO vector attached to TOPO TA cloning kit to obtain the plasmid pCR II/mBSSP2 containing the full length cDNA clone. The nucleotide sequence of DNA contained in this plasmid is shown in SEQ ID NO: 7 and the amino acid sequence of mSSP2 protein deduced from the nucleotide sequence is shown in SEQ ID NO: 8. Further, two different types of clones were obtained. The nucleotide sequences of these DNA are shown in SEQ ID NOS: 3 and 5, respectively. The amino acid sequences of mBSSP2 proteins deduced from these nucleotide sequences are shown in SEQ ID NOS: 4 and 6. These novel proteases are divided into types 1, 2 and 3. Type 1 is composed of 273 amino acids, type 2 is composed of 311 amino acids and type 3 is composed of 445 amino acids. These amino acid sequences contained the common amino acid sequence composed of 238 amino acids whose N-terminus side started with Ile-Val-Gly-Gly-Gln-Ala-Val (amino acid 1–7 of SEQ ID NO:2) as the mature serine protease. Further, in the amino acid sequence of the mature serine protease, a consensus sequence having a serine protease activity was contained. Furthermore, since there were two or more amino acid sequences specific for a sugar chain bonding site, it was presumed that the amino acid sequence had at least two sugar chains.

TABLE 1

| SEQ ID NO: | Name of primer | Direction | Sequence | Use |
|---|---|---|---|---|
| 22 | mBSSP2.0 | Forward | ATGGTGGAGAAGATCATTCCT | RACE |
| 23 | mBSSP2.1 | Forward | TACAGTGCCCAGAACCATG | RACE |
| 24 | mBSSPF4 | Forward | CTCAACTCTCTGCTAGACCG | RACE |
| 25 | mBSSP2F5 | Forward | ATAGTTGGCGGCCAAGCTGT | mature |
| 26 | mBSSPF7 | Forward | CCCAGCAGAACTTACTGCCT | FL* |
| 27 | mBSSP2.2 | Reverse | TGTTGCAGAGGTGGGTGCTG | RACE |
| 28 | mBSSP2R2 | Reverse | TACCATTGTGTCCTGCAGTGT | RACE |
| 29 | mBSSP2R5/E | Reverse | TGAATTCTGCTGCTTCTTCGGCTAGCG | FL* |

*: for full length

EXAMPLE 2

Expression mBSSP2 Gene in Mice Internal Organs

According to the protocol of QuickPrep Micro MRNA purification Kit (Amersham-Pharmacia), mRNAs were isolated from various internal organs of Balb/c mice or their fetuses. They were subjected to electrophoresis according to a conventional manner and transcribed to a nylon membrane. A probe was prepared separately by isolating a part of a nucleotide sequence encoding the mature protein of mBSSP2 from pCR II/mBSSP2, purifying it and labeling it with α-$^{32}$P dCTP. The probe was diluted with 5×SSC and reacted with the above membrane filter at 65° C. for a whole day and night. Then, the filter was washed twice each with 2×SSC/0.1% SDS at room temperature for 30 minutes, 1×SSC/0.1% SDS at room temperature for 30 minutes and 0.1×SSC/0.1% SDS at 65° C. for 30 minutes. The filter was exposed to an imaging plate for FLA2000 (Fuji Film) for one day to analyze the expression. The results shown in the drawings are those obtained by using mRNAs prepared from head of fetuses of mice and mRNAs prepared from brain of 5-day-, 10-day-, 14-day-, 18-day-, 30-day-, 3-month-, 7-month and 1-year-old mice (FIG. 1) and mRNAs prepared from various internal organs of 3-month-old mice (FIG. 2). In addition, the mRNAs of mice prepared above were subjected to RT-PCR by using Ready To Go RT-PCR Beads (Amersham-Pharmacia) and mBSSP2 gene specific primers (SEQ ID NOS: 25 and 29) according to the protocol attached to the kit.

As seen from FIGS. 1 and 2, in the case of northern blotting analysis, the expression of mBSSP2 was recognized in the head of 15th to 20th day fetuses of mice and, as to the 3-month-old mice, the expression was recognized in the prostate and testicle. Further, according to the results of RT-PCR, the expression was recognized in the head of 12-day-old mice and the testicle of 3-month-old mice.

EXAMPLE 3

Expression of Novel Serine Protease Mature Protein Encoded by mBSSP2 Gene (1) Construction of Expression Plasmid A cDNA region encoding the mature protein of BSSP2 protein was amplified by PCR using the plasmid pCR II/mBSSP2 as a template (the sequence of the 1st to 717th bases of SEQ ID NO: 1 was amplified by using the primers having the sequences represented by SEQ ID NOS: 25 and 29). The PCR product was ligated to pTrc-HisB (Invitrogen) which had been digested with BamHI and blunted with mung bean nuclease. E. coli JM109 was transformed by the resultant and colonies formed were analyzed by PCR to obtain E. coli containing the desired serine protease expressing plasmid pTrcHis/mBBSP2.

The resultant E. coli was designated E. coli pTrcHis/mBSSP2 and deposited at National Institute of Bioscience and Human-Technology (NIBH), Agency of Industrial Science & Technology of 1-1-3 Higashi, Tsukuba-shi, Ibaraki-ken, Japan on Oct. 29, 1998 under the accession numbers of FERM P-17033.

(2) Expression of Protein by E. coli Containing Expression Plasmid

A single colony of E. coli having the expression plasmid was inoculated in 10 ml of LB (Amp$^+$) culture medium and incubated at 37° C. overnight. This was inoculated in 250 ml of LB (Amp$^+$) culture medium and incubated at 37° C. When the absorbance at 600 nm became 0.5, 250 µl of 0.1 M IPTG (isopropyl-β-D-(-)-thiogalactopyranoside) was added and the incubation was continued for additional 5 hours. The E. coli was centrifuged and suspended in a cell disruption buffer (10 mM phosphate buffer pH 7.5, 1 mM EDTA) and sonicated on ice to disrupt E. coli. This was centrifuged at 14,000 r.p.m. for 20 minutes to obtain a precipitate. The precipitate was washed twice with a cell disruption buffer containing 0.5% Triton X-100™ and washed with water to remove Triton X-100™. Then, the resultant mixture was dissolved by soaking in a denaturation buffer containing 8 M urea (8M urea, 50 mM Tris pH8.5, 20 mM 2ME) at 37° C. for 1 hour. The solution was passed through TALON metal affinity resin (Clontech), washed with the denaturation buffer containing 10 mM imidazole, and then eluted with the denaturation buffer containing 100 mM imidazole to purify the solution. The purified product was dialyzed against PBS for 3 days with exchanging the buffer every other night to obtain the protein mBSSP2-His.

EXAMPLE 4

Expression of Novel Serine Protease Mature Protein Encoded by mBSSP2 Gene by Using pFBTrypSigTag/BSSP2

(1) Construction of pFBTrypSigTag/BSSP2

The sequences represented by SEQ ID NOS: 11 and 12 were subjected to annealing and digested with NheI and BamHI. The resultant fragment was inserted into pSecTag2A (Invitrogen) to obtain pSecTrypHis. Twenty units of BAmHI was added to 5 µg of pSecTrypHis vector and the vector was cleaved at 37° C. over 4 hours. Then, 6 units of mung bean nuclease (TAKARA) was added thereto and reacted at room temperature (25° C.) for 30 minutes to blunt the terminal ends. Further, the 3'-terminus side of the cloning site was digested cleaved with 20 units of XhoI, 1 unit of bacterial alkaline phosphatase (TAKARA) was added thereto and the reaction was carried out at 65° C. for 30 minutes.

Figure 3:
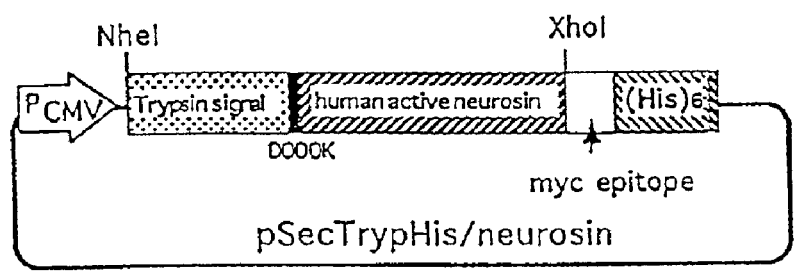
FIG. 3 is a plasmid constructed by the method of Example 4 hereinafter.

According to the same manner as that described in JP 9-149790 A or Biochim. Biophys. Acta, 1350, 11, 1997, mRNA was prepared from COLO201 cells and cDNA was synthesized to obtain the plasmid pSPORT/neurosin. cDNA of an active region of neurosin was obtained from pSPORT/neurosin by PCR using primers having the sequences represented by SEQ ID NOS: 13 and 14. Ten units of XhoI was reacted with the PCR product at 37° C. for 3 hours to cleave XhoI site at the 3'-side thereof. This was inserted into pSecTrypHis by TAKARA ligation kit to obtain pSecTrypHis/neursoin (FIG. 3).

Amplification was carried out by using the primers having the sequences represented by SEQ ID NOS: 15 and 16 so that the peptide of Leu-Val-His-Gly (SEQ ID NO:43) was present at the C-terminus of the part from trypsin signal to the enterokinase recognition site of pSecTrypHis/neurosin. This was inserted between NheI and HindIII sites of pSecTag2A to construct the plasmid pTrypSig.

One µg (0.1 µl) of the plasmid pSecTab2A was treated with the restriction enzymes NheI and BamHI to completely remove a region encoding the leader sequence of IgGk. One hundred pmol portions of DANs represented by SEQ ID NOS: 40 and 41 were added to the resultant solution and the mixture was heated at 70° C. for 10 minutes and subjected to annealing by allowing to stand at room temperature for 30 minutes. Two µl of I solution of DNA ligation kit Ver. 2 (TAKARA) was added to 1 µl portions of His secretory signal sequence treated by NheI and BamHI and pSecTag2A and the reaction was carried out at 16° C. for 30 minutes.

To the reaction mixture was add 0.1 ml of E. coli competent cell XL1-Blue (STRATAGENE) and reacted on ice for 30 minutes. Then, the reaction mixture was subjected to heat shock at 42° C. for 60 seconds. After standing on ice for 2 minutes, 0.9 ml of SOC culture medium (Toyo Boseki K.K.) was added thereto and the mixture was shaken with a shaker at 37° C. for 1 hour. The mixture was centrifuged at 5,000 r.p.m. for 1 minutes and the supernatant was discarded. The precipitated competent cells were suspended in the liquid remained in the centrifuge tube and the suspension was applied to 2 ampicillin LB plates containing 100 ug/ml of ampicillin in the ratio of 1:10. The plates were incubated at 37° C. for one night. Among the colonies formed, a colony into which DNA of His secretory signal was inserted was selected by PCR to obtain pTrypHis.

Figure 4:
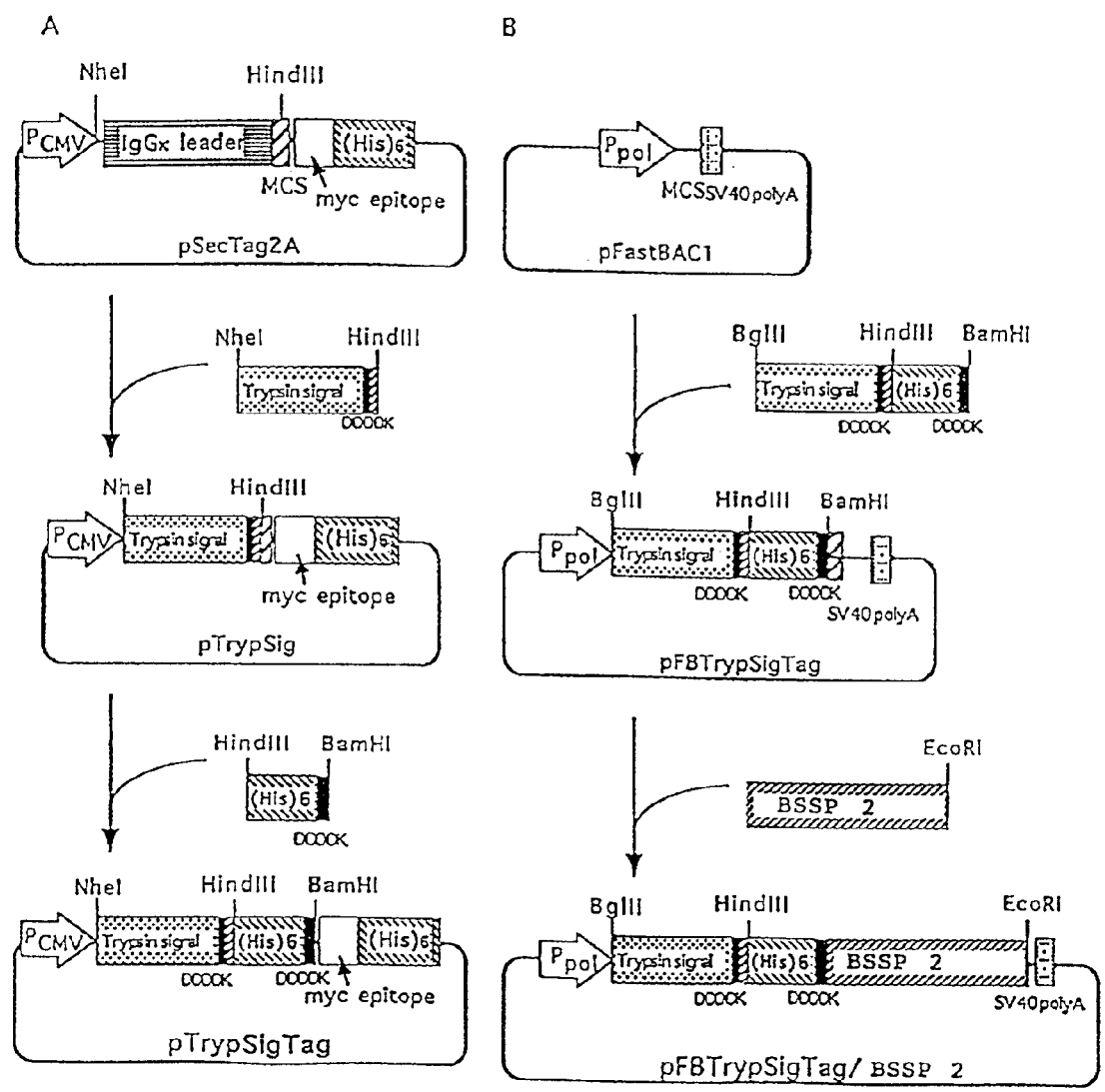
FIG. 4 illustrates the construction of plasmid pFBTrypSigTag/BSSP2 according to the method of Example 4 hereinafter.

A sequence of about 200 bp containing His Tag region of pTrypHis was amplified by using primers having the sequence represented by SEQ ID NOS: 16 and 17 and a fragment of about 40 bp containing His Tag and enterokinase recognizing site formed by digestion of HindIII and BamHI was inserted into pTrypSig to construct pTrypSig-Tag (FIG. 4A).

cDNA was prepared by PCR of the sequence from trypsin signal to enterokinase recognizing site of pTrypSigTag using primers having the sequences represented by SEQ ID NOS 14 and 18 and cut out by digestion with BglII and BamHI. It was inserted into BamHI site of pFastBAC1. The insertion direction was confirmed by PCR using primers having the sequences represented by SEQ ID NOS: 14 and 19. A clone into which the cDNA was inserted in the direction toward transcription and translation was selected to obtain pFB-TrypSigTag.

Twenty units of BamHI was added to 5 µg of pFB-TrypSigTag vector and the vector was cleaved at 37° C. over 4 hours, followed by addition of 6 units of mung bean nuclease (TAKARA) and reaction at room temperature (25° C.) for 30 minutes to blunt the terminal ends. Further, the 3'-side of the cloning site was cleaved by 20 units of EcoRI, followed by addition of 1 unit of bacterial alkaline phosphatase (TAKARA). The reaction was carried out at 65° C. for 30 minutes.

cDNA of the active region of mBSSP2 was obtained by PCR according to a conventional manner using pTrcHis/mBSSP2 or pCRII/mBSSP2 prepared from *E. coli* pTrcHis/mBSSP2 (accession No. FERM P-17033). The resultant cDNA was inserted into pFBTrypSigTag to obtain pFBTrypSigTag/mBSSP2 (FIG. 4B). At this time, correct insertion of mBSSP2 was confirmed by determining the sequence.

Bacmid DNA was transformed with PFBTrypSigTag/mBSSP2 according to a protocol of Gibco BRL BAC-TO-BAC baculovirus expression system to prepare a recombinant bacmid having chimera BSSP2 fused with trypsinogen signal peptide, HisTag and enterokinase recognizing site. When this was expressed in Sf-9 cell according to a manual of BAC-TO-BAC baculovirus expression system, it was secreted in the culture supernatant from 2 days after infection of the virus.

(2) Determination of Enzyme Activity

The recombinant fused protein mSSP2 obtained in the culture supernatant was passed through a chelate column to purify it and, after dialysis, its enzyme activity was determined. First, the culture supernatant was applied to a chelate column (Ni-NTA-Agarose, Qiagen) with PBS buffer and eluted stepwise with a solution of imidazole (Wako Pure Chemical Industries, Ltd.) dissolved in PBS. The resultant imidazole-eluted fraction was applied to a PD-10 column (Pharmacia) to exchange to PBS buffer. Fifty μl of this sample was mixed with 10 μl of enterokinase (1 U/1 μl, Invitrogen) and the reaction was carried out at room temperature for 60 minutes. Each of various synthetic substrates (Peptide Laboratory, Boc-Gln-Ala-Arg-MCA, Boc-Phe-Ser-Arg-MCA, Bz-Arg-MCA, Boc-Val-Leu-Lys-MCA, Pyr-Gly-Arg-MCA, Pro-Phe-Arg-MCA, Boc-Val-Pro-Arg-MCA, Z-Arg-Arg-MCA, Arg-MCA, Z-Phe-Arg-MCA) was dissolved in DMSO and diluted with 1 M Tris-HCl (pH 8.0) to obtain a substrate solution. Fifty μl of 0.2 M substrate solution was added thereto and further the reaction was carried out at 37° C. After one hour, the fluorescence of AMC (7-amino-4-methylcoumalin) formed by the enzymatic reaction was measured at 380 nm of excitation wavelength and 460 nm of fluorescence wavelength to determine the activity.

As a result, the recombinant fused protein mBSSP2 has been shown to have serine protease activity.

EXAMPLE 5

Cloning of hBSSP2 Gene

Reverse transcription of 1 μg of mRNA of human fetus brain (Clontech) was carried out by using Superscript II (Gibco BRL) and oligo dT-Not I primer (5' GGC-CACGCGTCGACTAGTA C(T)$_{17}$ 3' SEQ ID NO:44) to obtain cDNA. By using this as a template, PCR was carried out with primes prepared from mBSSP2 nucleotide sequence and represented by SEQ ID NOS: 30 and 31 to obtain a cDNA fragment of hBSSP2. Namely, 5 μl of the template, 5 μl of 10×ExTaq buffer (TAKARA), 5 μl of dNTPs, 10 pmol portions of the above primers and 0.5 μl of ExTaq (TAKARA) were adjusted to 50 μl with sterilized water and PCR was carried out by repeating a cycle of heating at 94° C. for 0.5 minute, at 55° C. for 0.5 minute and then at 72° C. for 1 minute, 35 times. The PCR reactions described hereinafter were carried out according to the same manner as the above composition and conditions except the template and primers. The PCR product was mixed with pGEM-T Easy vector (Promega) and Takara Ligation Solution I (TAKARA) and the reaction was carried out at 16° C. for 2 hours. Then, according to the same manner, *E. coli* JM109 was transformed and applied to a LB (Amp$^+$) plate. A plasmid was extracted from each colony formed according to a conventional manner and its nucleotide sequence was determined by dideoxy method. As for a clone having homology to mBSSP2, full length cDNA was obtained by 5' RACE and 3' RACE and its sequence was determined as described above. PCR was carried out by using the above cDNA as a template and primers having the sequences represented by SEQ ID NOS: 30 and 37. 3' RACE was carried out by PCR using a 1/100 dilution of the above PCR product as a template and primers having the sequences represented by SEQ ID NOS: 32 and 37. As for 5' RACE, cDNA for RACE was prepared from human fetal brain mRNA (Clontech) by using Superscript II and SMART RACE cDNA amplification kit (Clontech). PCR of this cDNA was carried out by using a primer of 10× Universal Primer Mix (attached to the kit) and a primer having the sequence represented by SEQ ID NO: 33. Further, PCR was carried out by using the 1/100 dilution of the latter PCR product, a template, Nested PCR Primer (attached to the kit) and a primer having the sequence represented by SEQ ID NO: 34. The finally obtained PCR product was subjected to TA cloning as described above and the nucleotide sequence was determined to obtain the upstream and downstream regions of the above clone. In addition, primers for amplifying the full length cDNA as represented by SEQ ID NOS: 35 and 36 were prepared based on the resultant nucleotide sequence and PCR was carried out by using the above synthetic cDNA as a template. This PCR product was cloned into pGEM-T Easy vector to obtain the plasmid pGEM-TE/hBSSP2 containing the full length cDNA clone. The DNA sequence contained in this plasmid is shown in SEQ ID NO: 9 and hBSSP2 protein deduced from the nucleotide sequence is shown in SEQ ID NO: 10.

*E. coli* containing this plasmid was designated E. coli pGEM-TE/hBSSP2 and deposited at National Institute of Bioscience and Human-Technology (NIBH), Agency of Industrial Science & Technology of 1-1-3 Higashi, Tsukuba-shi, Ibaraki-ken, Japan on Jul. 27, 1999 under the accession numbers of FERM P-17487.

TABLE 2

| SEQ ID NO: | Name of primer | Direction | Sequence | Use |
| --- | --- | --- | --- | --- |
| 30 | BSSP2SPF | Forward | ACTGCTGCCCACTGCATG | for part |
| 31 | BSSP2SPR | Reverse | CAGGGGTCCCCCGCTGTCTCC | for part |
| 32 | hBSSP2F11 | Forward | GCTCTCAACTTCTCAGACAC | RACE |
| 33 | hBSSP2R12 | Reverse | ACTCAGCTACCTTGGCGTAG | RACE |

TABLE 2-continued

| SEQ ID NO: | Name of primer | Direction | Sequence | Use |
|---|---|---|---|---|
| 34 | hBSSP2R11 | Reverse | CCTGGAGCATATCCGAGCTG | RACE |
| 35 | hBSSR2F12 | Forward | GCTTTACAACAGTGCTAC | WB* |
| 36 | hBSSP2R13/E | Reverse | TGGAATTCGAGGAAACAGCAGGACTCAG | WB* |
| 37 | | | TACTAGTCGACGCGTGGCC | |

*: whole body

EXAMPLE 6

Detection of hBSSP2 mRNA by Northern Blotting

Poly A+RNA extracted from respective tissues of human adults and fetuses were blotted on a membrane (Clontech) and the membrane was subjected to northern hybridization with a hBSSP2 probe. The probe was labeled by Takara BcaBEST random labeling kit (TAKARA) according to random priming method using a cDNA fragment which was amplified by using the full length of hBSSP2 as a template and the sequences represented by SEQ ID NOS: 34 and 35 as primers. The hybridization was carried out at 60° C. overnight and the filter was finally washed with 0.1×SSC and 0.1% SDS. The radioactivity was detected by FLA-2000 (Fuji Film). The signal corresponding to the adult brain was recognized at about 2.4 kb, the signal corresponding to the adult skeletal muscle was recognized at 7 kb and 1.3 kb and further the signal of the fetus liver was recognized at 7 kb (FIG. 5). The signal of the adult brain is considered to correspond to the exact nucleotide sequence and the others are considered to correspond to polymorphic forms resulted from the difference in splicing.

EXAMPLE 7

Figure 6:
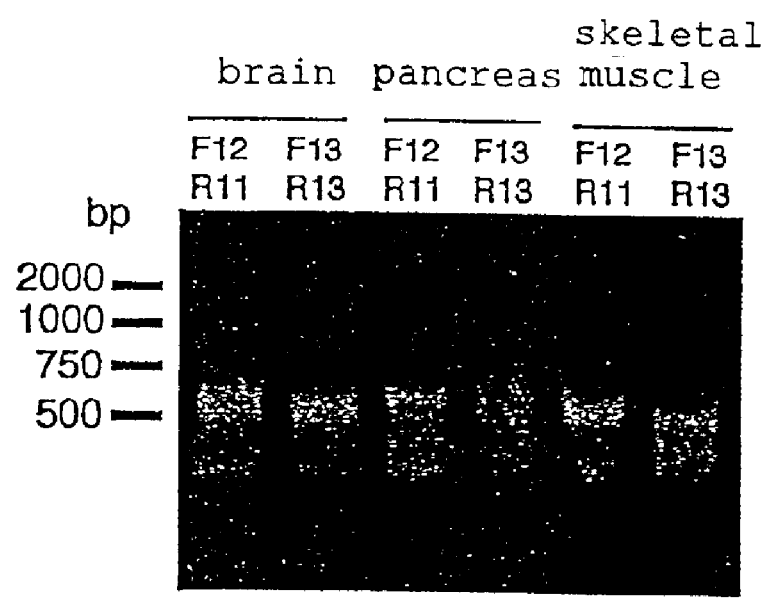
FIG. 6 illustrates the detection of hBSSP2 mRNA by RT-PCR.

Detection of hBSSP2 mRNA by RT-PCR mRNAs of human tissues purchased from Clontech were subjected to RT-PCR against hBSSP2 by using Ready To Go RT-PCR Beads (Amersham-Pharmacia) according to the protocol attached to the kit. Expression of hBSSP2 was recognized in brain and skeletal muscle (FIG. 6). No clear band was obtained in pancreas due to the combination of primers. This is considered to be non-specific amplification by a large amount of a serine protease present in pancreas.

EXAMPLE 8

Expression of hBSSP2 by Baculovirus System

Figure 7:
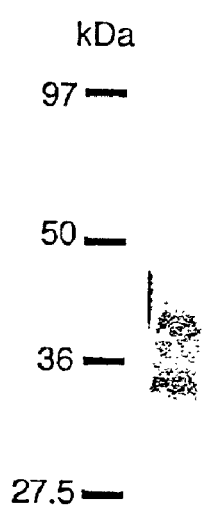
FIG. 7 illustrates the expression of hBSSP2 by a baculovirus system.

The signal sequence of human trypsinogen 2 and (His) 6 Tag and a sequence encoding the cleavage site of enterokinase were inserted into pFastBac1 (Gibco BRL) to obtain the plasmid pFBTrypSigTag. The mature form of hBSSP2 was inserted into the plasmid pFBTrypSigTag so that it was located in the flame (FIG. 4B). The mature form of hBSSP2 amplified by the sequences represented by SEQ ID NOS: 38 and 36 was cleaved by EcoRI and, according to the same manner as described with respect to mBSSP2, it was inserted into pFBTrySigTag to construct pFastBacTrypSigTag/hBSSP2. At this time, correct insertion of BSSP2 was confirmed by determining the nucleotide sequence by using the fluorescent labeled sequence represented by SEQ ID NO: 39. Bacmid DNA was transformed with PFBTrypSigTag/hBSSP2 according to a protocol of Gibco BRL BAC-TO-BAC baculovirus expression system to prepare a recombinant bacmid having chimera BSSP2 fused with trypsinogen signal peptide, HisTag and enterokinase recognizing site. When this was expressed in Sf-9 cell according to a manual of BAC-TO-BAC baculovirus expression system and the culture supernatant from 3 days after infection of the virus subjected to western blot technique with anti-DDDDK antibody, a specific band was detected to confirm expression of hBSSP2 (FIG. 7).

TABLE 3

| SEQ ID NO: | Name of primer | Direction | Sequence | Use |
|---|---|---|---|---|
| 38 | hBSSP2F13 | Forward | ACTGCTGCCCACTGCATG | for part |
| 39 | FBTrypSigTagF5 | | GCGCTAGCAGATCTCCATGAATCTACTCCTGATCC | NS* |

*: nucleotide sequence

INDUSTRIAL UTILITY

According to the present invention, there are provided isolated human and mouse serine protease (hBSSP2 and mBSSP2) polynucleotides, their homologous forms, mature forms, precursors and polymorphic variants. Further, according to the present invention, there are provided hBSSP2 and mBSSP2 proteins as well as compositions containing hBSSP2 and mBssP2 polynucleotides and proteins, their production and use.

SEQUENCE LISTING FREE TEXT

SEQ ID NO: 11: Designed oligonucleotide to construct plasmid pSecTrypHis.

SEQ ID NO: 12: Designed oligonucleotide to construct plasmid pSecTrypHis.

SEQ ID NO: 13: Designed oligonucleotide primer to amplify neurosin-encoding sequence.

SEQ ID NO: 14: Designed oligonucleotide primer to amplify neurosin-encoding sequence.

SEQ ID NO: 15: Designed oligonucleotide primer to amplify a portion of plasmid pSecTrypHis/Neurosin.

SEQ ID NO: 16: Designed oligonucleotide primer to amplify a portion of plasmid pSecTrypHis/Neurosin.

SEQ ID NO: 17: Designed oligonucleotide primer to amplify a portion of plasmid pTrypHis.

SEQ ID NO: 18: Designed oligonucleotide primer to amplify a portion of plasmid pTrypSigTag.

SEQ ID NO: 19: Designed oligonucleotide primer to amplify a portion of plasmid pFBTrypSigTag.

SEQ ID NO: 20: Designed oligonucleotide primer to amplify conserved region of serine proteases-encoding sequence; n is a, c, g or t.

SEQ ID NO: 21: Designed oligonucleotide primer to amplify conserved region of serine proteases-encoding sequence; n is a, c, g or t.

SEQ ID NO: 22: Designed oligonucleotide primer designated as mBSSP2.0 for RACE for mBSSP2 (forward).

SEQ ID NO: 23: Designed oligonucleotide primer designated as mBSSP2.1 for RACE for mBSSP2 (forward).

SEQ ID NO: 24: Designed oligonucleotide primer designated as mBSSPF4 for RACE for mBSSP2 (forward).

SEQ ID NO: 25: Designed oligonucleotide primer designated as mBSSP2F5 to amplify mature mBSSP2-encoding region (forward).

SEQ ID NO: 26: Designed oligonucleotide primer designated as mBSSPF7 to amplify full-length mBSSP2-encoding MRNA (forward).

SEQ ID NO: 27: Designed oligonucleotide primer designated as mBSSP2.2 for RACE for mBSSP2 (reverse).

SEQ ID NO: 28: Designed oligonucleotide primer designated as mBSSP2R2 for RACE for mBSSP2 (reverse).

SEQ ID NO: 29: Designed oligonucleotide primer designated as mBSSP2R5/E to amplify full-length mBSSP2-encoding MRNA (reverse).

SEQ ID NO: 30: Designed oligonucleotide primer designated as BSSP2SPF to amplify a portion of hBSSP2 (forward).

SEQ ID NO: 31: Designed oligonucleotide primer designated as BSSP2SPR to amplify a portion of hBSSP2 (reverse).

SEQ ID NO: 32: Designed oligonucleotide primer designated as hBSSP2F11 for RACE for hBSSP2 (forward).

SEQ ID NO: 33: Designed oligonucleotide primer designated as hBSSP2R12 for RACE for hBSSP2 (reverse).

SEQ ID NO: 34: Designed oligonucleotide primer designated as hBSSP2R11 for RACE for hBSSP2 (reverse).

SEQ ID NO: 35: Designed oligonucleotide primer designated as hBSSP2F12 to amplify full length hBSSP2 (forward).

SEQ ID NO: 36: Designed oligonucleotide primer designated as hBSSP2R13/E to amplify full length hBSSP2 (reverse).

SEQ ID NO: 37: Designed oligonucleotide primer for RACE for hBSSP2.

SEQ ID NO: 38: Designed oligonucleotide primer designated as hBSSP2F13 to amplify a portion of hBSSP2 (forward).

SEQ ID NO: 39: Designed oligonucleotide primer designated as FBTrpsigtagF5 to detect hBSSP2.

SEQ ID NO: 40: Designed oligonucleotide to construct plasmid pTrypHis.

SEQ ID NO: 41: Designed oligonucleotide to construct plasmid pTrypHis.

---

What is claimed is:

1. An isolated protein selected from the group consisting of:
   (a) a protein having the amino acid sequence of 240 amino acids identified by amino acid residues 218–457 of SEQ ID NO:10 and having serine protease activity; and
   (b) a protein having the amino acid sequence of 457 amino acids identified by amino acid residues 1–457 of SEQ ID NO:10.

2. The protein of claim 1 having the amino acid sequence of 240 amino acids represented identified amino acid residues 218–457 of SEQ ID NO: 10.

3. The protein of claim 1 having the amino acid sequence of 457 amino acids represented identified amino acid residues 1–457 of SEQ ID NO:10.

* * * * *